(12) United States Patent
Papsidero et al.

(10) Patent No.: US 6,723,518 B2
(45) Date of Patent: Apr. 20, 2004

(54) DETECTION AND TREATMENT OF BREAST DISEASE

(75) Inventors: Lawrence D. Papsidero, Orchard Park, NY (US); Lyn M. Dyster, Lewiston, NY (US); Jana M. Frustaci, Williamsville, NY (US)

(73) Assignee: Codon Diagnostics, LLC, Amherst, NY (US)

( * ) Notice: Subject to any disclaimer, the term of this patent is extended or adjusted under 35 U.S.C. 154(b) by 0 days.

(21) Appl. No.: 09/834,795

(22) Filed: Apr. 13, 2001

(65) Prior Publication Data

US 2002/0076710 A1 Jun. 20, 2002

Related U.S. Application Data

(62) Division of application No. 09/146,580, filed on Sep. 3, 1998, now Pat. No. 6,306,653.
(60) Provisional application No. 60/071,899, filed on Jan. 20, 1998, and provisional application No. 60/092,155, filed on Jul. 9, 1998.

(51) Int. Cl.[7] .................. G01N 33/53; G01N 33/567; G01N 33/537; G01N 33/566; A61K 39/395
(52) U.S. Cl. .................. 435/7.1; 435/7.2; 435/7.21; 435/7.23; 435/7.24; 435/7.92; 435/7.91; 436/501; 436/503; 436/63; 436/64; 424/130.1
(58) Field of Search .................. 435/7.1, 7.2, 7.21, 435/7.23, 7.24, 7.92, 7.91; 436/501, 503, 64, 63; 424/130.1

(56) References Cited

FOREIGN PATENT DOCUMENTS

| WO | 98/23750 | 6/1998 |
| WO | 99/06439 | 2/1999 |
| WO | 99/06549 | 2/1999 |

OTHER PUBLICATIONS

U.S. patent application Ser. No. 09/834,794, Papsidero et al., filed Apr. 13, 2001.
Skipski et al., "A New Proteolipid Apparently Associated with Cancer," *Proc. Soc. Exp. Biol. Med.*, 136:1261–1264.
Kleinberg, "Human α–Lactalbumin: Measurement in Serum and in Breast Cancer Organ Cultures By Radioimmunoassay,", *Science*, 190:276–278 (1975).
Franchimont et al., "Simultaneous Assays of Cancer Associated Antigens in Benign and Malignant Breast Diseases," *Cancer*, 39:2806–2812 (1977).
Kloppel et al., "Glycolipid–Bound Sialic Acid in Serum: Increased Levels in Mice and Humans Bearing Mammary Carcinomas," *Proc. Natl. Acad. Sci, U.S.A.*, 74:3011–3013 (1977).
Ip et al., "Alterations in Serum Glycosyltransferases and 5'–Nucleotidase in Breast Cancer Patients," *Cancer Res.*, 38:723–728 (1978).
Dao et al., "Serum Sialytransferase and 5'–Nucleotidase as Reliable Biomarkers in Women with Brest Cancer," *J. Natl. Cancer Inst.*, 65(3):529–534 (1980).
Taylor–Papadimitriou et al. "Monoclonal Antibodies to Epithelium–Specific Components of the Human Milk Fat Globule Membrane: Production and Reaction with Cells in Culture," *Int. J. Cancer*, 28:17–21 (1981).
Weir et al., "Human Kappa–Casein as a Tumor Marker: Purification and Properties," *Cancer Detect. Prev.*, 4:193–204 (1981).
Ceriani et al., "Circulating Human Mammary Epithelial Antigens in Breast Cancer," *Proc. Natl. Aca. Sci. U.S.A.*, 79:5420–5424 (1982).
Barry et al., "Correlation of Immunohistochemical Markers with Patient Prognosis in Breast Carcinoma: A Quantitative Study," *Am. J. Clin. Pathol.*, 82:582–585 (1984).
Burchell et al., "Detection of the Tumour–Associated Antigens Recognized by the Monoclonal Antibodies HMFG–1 and 2 in Serum from Patients with Breast Cancer," *Int. J. Cancer*, 34:763–768 (1984).
Papsidero et al., "Expression of Ductal Carcinoma Antigen in Breast Cancer Sera as Defined Using Monoclonal Antibody F36/22," *Cancer Res.*, 44:4653–4657 (1984).
Hayes et al., "Use of a Murine Monoclonal Antibody for Detection of Circulating Plasma DF3 Antigen Levels in Breast Cancer Patients," *J. Clin. Invest.*, 75:1671–1678 (1985).
Bartkova et al., "Lack of β–Casein Production by Human Breast Tumours Revealed by Monoclonal Antibodies," *Eur. J. Cancer Clin. Oncol.*, 23:1557–1563 (1987).
Cohen et al., "Tumor–Associated Antigens in Breast Carcinomas," *Cancer*, 60:1294–1298 (1987).
Earl et al., "Immunohistochemical Study of β– and κ–Casein in the Human Breast and Breast Carcinomas, Using Monoclonal Antibodies," *Cancer Res.*, 49:6070–6076 (1989).
de Almeida et al., "Immunohistochemical Markers in the Identification of Metastatic Breast Cancer," *Breast Cancer Res. Treat.*, 21:201–210 (1992).

(List continued on next page.)

*Primary Examiner*—Susan Ungar
(74) *Attorney, Agent, or Firm*—Darby & Darby

(57) ABSTRACT

An isolated chemokine is disclosed. The isolated chemokine is expressed preferentially in breast tissue or can be detected in breast milk. It includes from about 100 to about 132 amino acids, has a deduced molecular weight of from about 10 to about 16 kDa, and has a deduced isoionic point of from about pH 10.1 to about pH 10.7. Antibodies and binding portions thereof recognizing the subject chemokine and peptides which include the antigenic portions of the subject chemokines are described. DNA molecules which encode the subject chemokines as well as nucleic acid molecules which, under stringent conditions, hybridize to nucleic acid molecules encoding the subject chemokines or to a complement thereof are also disclosed. The chemokines, peptides, antibodies and binding portions thereof, and nucleic acid molecules can be used to detect and treat breast disease, such as inflammations, infections, mastitis, benign cystitis, benign hyperplasias, cancer and other malignancies as well as other pathological states of the mammary gland.

7 Claims, 1 Drawing Sheet

OTHER PUBLICATIONS

Skilton et al., "Characterization of Monoclonal Antibodies Reactive with Normal Resting, Lactating and Neoplastic Human Breast," *Tumor Biol.*, 11:20–38 (1990).

Watson et al., "Mammaglobin, a Mammary–Specific Member of the Uteroglobin Gene Family, Is Overexpressed in Human Breast Cancer," *Cancer Res.*, 56:860–865 (1996).

EMBL Database, ID HS459102, Accession No. R38459, May 6, 1995.

EMBL Database, ID HS300256, Accession No. N20300, Dec. 23, 1995.

Goldman et al., "Spectrum of Immunomodulating Agents in Human Milk," *Intl. J. Pediatric Hematology/Oncology*, 4(5):491–497 (1997).

Srivastava et al., "Cytokines in Human Mil," *Research Communications in Molecular Pathology and Pharmacology*, 93(3):263–287 (1996).

Figure 1

```
MACK      MQQRGLAIVA LAVCA--AL  HASEAILPIA SS-CCTEVSHH ISRRLLERV  NMCRIQRADG DCDLAAVILH VKRXR--ICV
HTECK     M---NIWLLA CLVAGFLGAW APAVHTQGVF ED-CCLAYHYP IGWAVLRRA  WTYRIQEVSG SCNLPAAIFY LPKRHRKVCG
LARC      MCCTKSLLLA ALMSVLL--L HLCGESEASN FD-CCLGY--T DRILHPKFI  VGFTRQLANE GCDINAIIF- HTKKKLSVCA
TARC      MAPLKMLALVT LLLGASL--Q HIHAARGTNV GRECCLEY--F KGAIPLRKL  KTWYQ--TSE DCSRDAIVF- VTVQGRAICS
I309      MQITTALVCLLLAG M----WP--E DVDSKSMQVP FSRCCFSF--A EQEIPLRAI  LCY-R-NTSS ICSNEGLIF- KLKRGKEACA
MCP-2                AQPDSVSI   PITCCFNV--I NRKKIPIQRL ESYTR-ITNI  QCPKEAVIF- KTKRGKEVCA
MCP-4     MKVS-AVLLCLLLMT AAFNP----Q GLAQPDALNV PSTCCFTF--S SKKISLQRL KSYV--ITTS RCPQKAVIF- RTKLGKEICA
Eotaxin   MKVS-AALIWILLIA AAFSP----Q GLAGPASV-- PTTCCFNL--A NRKKIPIQRL ESYRR-ITSG KCPQKAVIF- KTKLAKDICA
MCP-3     MKAS-AALLCLLLTA AAFSP----Q GLAQPVGINT STTCCYRF--I NKKKIPKQRL ESYRR-TTSS HCPREAVIF- KTKLDKEDCA
MCP-1     MKVS-AALLCLLLTA AAFIP----Q GLAQPDAINA PVTCCYNF--T NRKISVQRL  ASYRR-ITSS KCPKEAVIF- KTIVAKEDCA
RANTES    MKVSAARLAV-ILIA TALCA----P ASASPYSSDT -TPCCFAY--I ARPLPRAHI  KEYFY--TSG KCSNPAVVF- VTRKNRQVCA
HCC-1     MKISVAAIPFFLLIT IALGT----K TESSSRGPYH PSECCFTY--T TYKIPRQRI  MDYYE--TNS QCSKPGIVF- ITKRGHSVCT
MIP-1B    MKLCVTVLSL-LMLV AAFCS----P ALSAPMGSDP PTACCFSY--T ARKLPRNFV  VDYYE--TSS LCSQPAVVF- QTKRSKQVCA
LB78B     MQVSTAALAV-LLCT MALCN----Q VLSAPLAADT PTACCFSY--T SRQIPQNFI  ADYFE--TSS QCSKPSVIF- LTKRGRQVCA
LD78A     MQVSTAALAV-LLCT MALCN----Q -FSASLAADT PTACCFSY--T SRQIPQNFI  ADYFE--TSS QCSKPGVIF- LTKRSRQVCA
PARC      MKGLAAALLV-LVCT MALC-----  --SCAQVGTN KELCCLVY--T SWQIPQKFI  VDYSE--TSP QCPKPGVIL- LTKRGRQDCA MACK      SPHNHTVKQW MKVQAAXKNG KGNVCHRKK- ----HHGKR  ETYGHKTP-  -------
HTECK     NPKSREVQRA MKLLLDARNKV FAKLHHNMQT FQAGPHAVKK NSNRAHQGKH ETYGHKTP- KRNVSLLISA NSGL......
LARC      NPKQTWV-KY I--------  ---------  ---------  LSSGNSKLSS SKFSNPISSS ---Y...... 
TARC      DPNNQRV-KN A--------  ---------  ---------  ---------  ---------  VRLLSKK VKNM......
I309      LDTVGWV-QR H--------  ---------  ---------  ---------  ---------  VKYLQSL ERS.......
MCP-2     DPKERWV-RD S--------  ---------  ---------  ---------  ---------  RKMLRHC PSKRK.....
MCP-4     DPKEKWV-QN Y--------  ---------  ---------  ---------  ---------  MKHLDQI FQNLKP....
Eotaxin   DPKKKWV-QD S--------  ---------  ---------  ---------  ---------  MKHLGRK AHTLKT....
MCP-3     DPTQKWV-QD P--------  ---------  ---------  ---------  ---------  MKYLDQK SPTPKP....
MCP-1     DPKQKWV-QD S--------  ---------  ---------  ---------  ---------  MKHLDKK TQTPKL....
RANTES    NPEKKWV-RE Y--------  ---------  ---------  ---------  ---------  MDHLDKQ TQTPKT....
HCC-1     NPSDKWV-QD Y--------  ---------  ---------  ---------  ---------  INSLEMS
MIP-1B    DPSESWV-QE Y--------  ---------  ---------  ---------  ---------  IKDMKEN
LB78B     DPSEEWV-QK Y--------  ---------  ---------  ---------  ---------  VYDLELN
LD78A     DPSEEWV-QK Y--------  ---------  ---------  ---------  ---------  VSDLELSA
PARC      DPNKKWV-QK Y--------  ---------  ---------  ---------  ---------  ISDLKLNA
```

DETECTION AND TREATMENT OF BREAST DISEASE

This application is a divisional application of U.S. patent application Ser. No. 09/146,580, filed Sep. 3, 1998 now U.S. Pat. No. 6,306,653, which claims the benefit of U.S. Provisional Patent Application Ser. No. 60/071,899, filed Jan. 20, 1998, now abandoned and U.S. Provisional Patent Application Ser. no. 60/092,155, filed Jul. 9, 1998, now abandoned which are hereby incorporated by reference.

FIELD OF THE INVENTION

The present invention relates to the detection and treatment of breast disease.

BACKGROUND OF THE INVENTION

Breast cancer is one of the largest classes of malignant disease in women. However, breast cancer presents inherent difficulties in regard to the ease with which it is detected and diagnosed. This is in contrast to detection of some other common cancers, including skin and cervical cancers, the latter of which is based on cytomorphologic screening techniques.

Early detection of breast cancer represents a compelling goal in oncology. Although techniques such as computerized tomography, mammography, and magnetic resonance imaging have greatly improved tumor surveillance over the past decade, there still remains a need for serologic and other blood-based assays.

Serologic assays are easily performed, inexpensive, and analytically-sensitive and can be serially run over time with relative ease. The essence of breast cancer screening, using tumor marker detection, is to efficiently identify a group of higher-risk individuals from within a large population. Thereafter, confirmatory testing is implemented to establish a diagnosis of malignancy.

There are several classifications of tumor markers possible, based upon the structure or biological function of the marker. Tumor marker classifications include tissue specific antigens (e.g., PSA, NSE, PAP, calcitonin, HCG), major histocompatibility complex ("MHC") antigens, viral antigens (e.g., HTLV-I gag protein), oncogene products (e.g., c-HER-2/Neu), oncofetal markers (e.g., CEA, AFP), hormones (e.g., thyroid hormones), enzymes (e.g., telomerase, galactosyltransferase), and altered glycoproteins/glycolipids (e.g., polymorphic epithelial mucins). It should be noted that these classification schemes are imprecise and contain redundancies. For example, calcitonin is an important serological marker for medullary carcinoma of the thyroid and may be classified not only as a hormone but also as a tissue specific protein of the thyroid. Likewise, PSA, HCG, thyroid hormones, PAP, and NSE are tissue specific proteins and also exhibit enzymatic or hormonal activities. Generally, tumor markers providing high clinical utility reside in the broadly defined tissue specific class. This class of tumor markers contains enzymes, isoenzymes, hormones, growth factors, and other molecules with biologic activity.

The importance of a tumor marker's being tissue specific is illustrated by one of the best known tumor antigens, carcinoembryonic antigen ("CEA"). When first discovered, CEA was thought to be specific to cancers of the digestive system. However, CEA has since been detected in normal adults as well as in patients with benign liver disease, such as alcoholic hepatitis or biliary obstruction. Because of the overall lack of specificity and sensitivity, there being no threshold difference in CEA levels that serves to separate benign from malignant conditions, CEA cannot be used in a general diagnostic test. Instead, it is principally used to monitor a patient's response to treatment.

To be useful in serologic assays, a tumor marker should be one that is released into the bloodstream as a circulating marker. Circulating antigens are now known to exist in breast cancer. Breast tissue markers, such as casein (Franchimont et al., *Cancer*, 39:2806–2812 (1977)) and α-lactalbumin (Kleinberg et al., *Science*, 190:276–278 (1975)) and purported cancer markers, such as glycosyl transferases (Ip et al., *Cancer Res.*, 38:723–728 (1978) and Dao et al., *J. Natl. Cancer Inst.*, 65:529–534 (1980)), glycolipids (Kloppel et al., *Proc. Natl. Acad. Sci. USA*, 74:3011–3013 (1977)), and phospholipids (Skipski et al., *Proc. Soc. Exp. Biol. Med.*, 136:1261–1264 (1971)) have all been used in various diagnostic techniques for breast cancer but have not gained widespread acceptance as breast cancer markers. More recently, circulating human mammary epithelial antigens have been proposed as specific markers for breast cancer (Ceriani et al., *Proc. Natl. Acad. Sci. USA*, 79:5420–5424 (1982)). Burchell et al., *Int. J. Cancer*, 34:763–768 (1984) describes monoclonal antibodies which detect high molecular weight mucin-like antigens elevated in patient serum. Hayes, *J. Clin. Invest.*, 75:1671–1678 (1985) also describes a monoclonal antibody that recognizes a high molecular weight mammary epithelial antigen present in elevated amounts in the plasma of breast cancer patients. See also Papsidero et al., *Cancer Res.*, 44:4653–4657 (1984) and Taylor-Papadimitriou et al., *Int. J. Cancer*, 28:17–28 (1981). Other breast tissue specific proteins or markers include alpha, beta, and kappa caseins, alpha-lactalbumin, lactoferrin, and selected epithelial membrane antigens. These are described in Cohen et al., *Cancer*, 60:1294–1298 (1987); Bartkova, *Eur. J. Cancer Clin. Oncol.*, 23:1557–1563 (1987); Weir et al., *Cancer Detect. Prev.*, 4:193–204 (1981); de Almeida et al., *Breast Cancer Res. Treat.*, 21:201–210 (1992); Skilton et al., *Tumor Biol.*, 11:20–38 (1990); Earl et al., *Cancer Res.*, 49:6070–6076 (1989); Barry et al., *Amer. J. Clin. Path.*, 82:582–585 (1984); and Watson et al., *Cancer Res.*, 56:860–865 (1996). None of these previously described antigens has been used as a basis for a widely accepted breast cancer clinical assay.

There have also been several attempts to develop improved methods of breast cancer detection and diagnosis based on oncogene mutations, gene amplification, and loss of heterozygosity in invasive breast cancer. These methods have not gained wide acceptance.

Despite the use of mammography and the development of some breast tissue specific markers, there still remains a need for simple and rapid methods for detecting breast cancer. The present invention is directed to meeting this need.

SUMMARY OF THE INVENTION

One aspect of the present invention relates to an isolated chemokine that is preferentially expressed in breast tissue or which can be detected in breast milk. The isolated chemokine includes about from about 100 to about 132 amino acids, has a deduced molecular weight of from about 10 to about 16 kDa, and has a deduced isoionic point of from about pH 10.1 to about pH 10.7.

The present invention also relates to peptides having an amino acid sequence corresponding to an antigenic portion of the subject chemokine, to antibodies which recognize this chemokine, and to isolated nucleic acid molecules which encode this chemokine.

The present invention also relates to an isolated nucleic acid molecule which, under stringent conditions, hybridizes to a nucleic acid molecule encoding a chemokine of the present invention or to a complement thereof.

In another aspect thereof, the present invention relates to an isolated nucleic acid molecule which encodes for a chemokine of the present invention.

The present invention also relates to a method for detecting breast disease in a patient. A sample of tissue or body fluid from the patient is contacted with a nucleic acid primer which, under stringent conditions, hybridizes to a nucleic acid molecule encoding a chemokine of the present invention or to a complement thereof. The sample of tissue or body fluid from the patient in contact with the nucleic acid primer is treated under conditions effective to amplify breast tissue specific nucleic acid molecules. The method further includes detecting the breast tissue specific nucleic acid molecules.

The present invention also relates to another method of detecting breast disease in a patient. In this method, a sample of tissue or body fluid from the patient is contacted with a nucleic acid probe under conditions effective to permit formation of a hybridization complex between the probe and breast tissue specific nucleic acid molecules. The nucleic acid probe is one which, under stringent conditions, hybridizes to a nucleic acid molecule encoding a chemokine of the present invention or to a complement thereof. The method further includes detecting the hybridization complex.

The present invention also relates to yet another method of detecting breast disease in a patient. The method includes providing an antibody or binding portion thereof which recognizes a chemokine of the present invention. The antibody or binding portion thereof is contacted with a liquid or tissue sample from the patient under conditions effective to permit binding of the antibody or binding portion thereof to the chemokine in the liquid or tissue sample. The method further includes detecting presence of antibody or binding portion thereof bound to the chemokine in the liquid or tissue sample.

The present invention, in another aspect thereof, relates to a method of treating breast disease in a patient. The method includes administering to the patient an effective amount of an antibody or binding portion thereof which recognizes a chemokine of the present invention.

The present invention also relates to another method of treating breast disease in a patient. The method includes administering to the patient an effective amount of a peptide which binds to a cellular receptor for a chemokine of the present invention.

The present invention also relates to a method of vaccinating a patient against breast disease. The method includes administering to the patient an effective amount of an antigenic portion of a chemokine of the present invention.

The chemokines, peptides, antibodies, and nucleic acid molecules of the present invention are useful in the early detection of various pathological states of the mammary gland, such as inflammations, infections, benign hyperplasias, and malignancies. In particular, they can be used in the early detection of breast cancer as well as for monitoring the presence or absence of metastatic breast cancer cells in a patient's tissues and fluids, such as blood, lymph nodes, bone marrow, and other sites of disease dissemination. They can also be used to stage patients with breast cancer and to assess the effects of conventional breast cancer therapies. Furthermore, the chemokines, peptides, and antibodies of the present invention can be used to treat or prevent breast disease.

BRIEF DESCRIPTION OF THE DRAWING

FIG. 1 is a series of aligned amino acid sequences of various members of the CC chemokine family and the amino acid sequence of a chemokine of the present invention. Members of the CC chemokine family that are shown are HTECK (SEQ ID NO:20), LARC (SEQ ID NO:21), TARC (SEQ ID NO:22), I309 (SEQ ID NO:23), MCP-2 (SEQ ID NO:24), MCP-4 (SEQ ID NO:25), Eotaxin (SEQ ID NO:26), MCP-3 (SEQ ID NO:27), MCP-1 (SEQ ID NO:28), RANTES (SEQ ID NO:29), HCC-1 (SEQ ID NO:30), MIP-1B (SEQ ID NO:31), LB78B (SEQ ID NO:32), LD78A (SEQ ID NO:33), and PARC (SEQ ID NO:34).

DETAILED DESCRIPTION OF THE INVENTION

The present invention relates to an isolated chemokine that is preferentially expressed in breast tissue or that is detectable in breast milk. Chemokine, as used herein, is meant to include proteins which are proinflammatory cytokines that are chemoattractants and activators of specific types of leukocytes. Further details with respect to chemokine activity can be found, for example, in U.S. Pat. No. 5,688,927 to Godiska et al. and Baggiolini et al., *Advances in Immunology,* 55:97–179 (1994), which are hereby incorporated by reference The chemokine may include a leader sequence, typically about 22 amino acids in length, or, alternatively, the leader sequence can be cleaved from the chemokine. The isolated chemokine preferably includes from about 100 to 132 amino acids, more preferably, from about 105 to about 127 amino acids, and, most preferably, about 105 or 127 amino acids. The deduced molecular weight of the chemokine of the present invention is preferably from about 10 to about 16 kDa, more preferably, from about 12 kDa to about 14 kDa, and preferably has a deduced isoionic point of from about pH 10.1 to about pH 10.7, more preferably about 10.4.

As indicated above, the chemokine of the present invention is preferentially expressed in breast tissue. That is, more chemokine of the present invention is expressed in breast tissue than in any other tissue in the body. More preferably, the chemokine of the present invention is expressed substantially exclusively or exclusively in breast tissue. That is, substantially all of the chemokine of the present invention is expressed in breast tissue. In addition or alternatively to being preferentially expressed in breast tissue, the chemokine of the present invention can be detected in breast milk, such as by using conventional protein detection methods.

One particularly preferred chemokine of the present invention has an amino acid sequence corresponding to SEQ ID NO:1, as follows:

MQQRGLAIVALAVCAALHASEAILPIASSCCTEVSHHISRRLLERVNMC

RIQRADGDCDLAAVILHVKRXRICVSPHNHTVKQWMKVQAAXKNGKGNV

CHRKKHHGKRNSNRAHQGKHETYGHKTPY

As indicated above, chemokine, as used herein, can include a leader sequence, or, alternatively, all or part of the leader sequence may be removed. In SEQ ID NO:1, approximately the first 22 amino acids represents the leader sequence. Thus, chemokines of the present invention can also have an amino acid sequence corresponding to, for example, SEQ ID NO:2, as follows:

```
LPIASSCCTEVSHHISRRLLERVNMCRIQRADGDCDLAAVILHVKRXRICV

SPHNHTVKQWMKVQAAXKNGKGNVCHRKKHHGKRNSNRAHQGKHETYGHK

TPY
```

The chemokine of the present invention is isolated (i.e., substantially free of the biological materials with which it is naturally found). In many applications, it is desirable that the chemokine of the present invention be purified (i.e., substantially free of all other biological materials). The chemokines of the present invention can be in monomer form, or they can be associated with other chemokines, such as in the form of dimers.

The present invention also relates to peptides which include an amino acid sequence corresponding to an antigenic portion of a chemokine of the present invention. In general, the size of the peptide antigen is not believed to be particularly crucial, so long as it is at least large enough to carry the antigenic core sequence or sequences. Generally, the smallest useful antigenic sequence is on the order or about six amino acids in length. However, the size of the antigen may be larger where desired, so long as it contains a basic antigenic core sequence.

Accordingly, through the use of computerized peptide sequence analysis program (DNAStar Software, DNAStar, Inc., Madison, Wis.), the portions of the peptide can be identified that are believed to constitute antigenic sequences which include particular epitopes of the protein. More particularly, antigenic portions of a chemokine of the present invention can be identified by hydropathy analysis, such as that described in Kyte et al., "A Simple Method for Displaying the Hydropathic Character of a Protein," *J. Mol. Biol.*, 157:105–132 (1982), which is hereby incorporated by reference.

Synthesis of peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptides synthesized in this manner may then be aliquoted in predetermined amounts and stored in conventional manners, such as in aqueous solutions or, even more preferably, in a powder or lyophilized state pending use.

Particularly preferred peptides of the present invention are those which include amino acid sequences corresponding to TEVSHHISRRLLERVNMC (SEQ ID NO:3), KNGKGN-VCHRKKHHGK (SEQ ID NO:4), and NSN-RAHQGKHETYGHKTPY (SEQ ID NO:5).

As described below, the chemokines or peptides of the present invention can be used to raise antibodies that recognize chemokines of the present invention. The chemokines and peptides of the present invention can also be administered alone or in combination with a pharmaceutically-acceptable carrier to patients, as a vaccine, for preventing breast disease.

The present invention also relates to antibodies and binding portions thereof which recognize a chemokine according to the present invention. Preferably, the antibody or binding portion thereof also recognizes particular antigenic portions of the subject chemokine, such as peptides having amino acid sequences corresponding to SEQ ID NO:3, SEQ ID NO:4, and SEQ ID NO:5.

The antibodies and binding portions thereof can be used to detect breast disease in a patient. As used herein, breast disease is meant to include various pathological states of the mammary gland, such as inflammations, infections, mastitis, benign cystitis, benign hyperplasias, and cancer and other malignancies. Detection of breast disease involves providing an antibody or binding portion thereof which recognizes a chemokine of the present invention. The antibody or binding portion thereof is contacted with a tissue or fluid sample from the patient under conditions effective to permit binding of the antibody or binding portion thereof to chemokine that is present in the tissue or fluid sample to form a complex. The presence of a chemokine of the present invention in the tissue or fluid sample is detected by detecting the complex.

Such contacting can be carried out in vivo in a living patient. In this embodiment of the present invention, the antibody or binding portion thereof is administered (e.g., orally or parenterally) to the patient under conditions effective to permit binding of the antibody or binding portion thereof to the chemokine of the present invention in the in vivo tissue or fluid sample. Using this method, patients can be screened for breast diseases associated with the presence of chemokines of the present invention. Alternatively, the method can be used to identify the recurrence of such diseases, particularly when the disease is localized in a particular biological material of the patient. For example, recurrence of breast disease in a patient's breast tissue can be detected by administering a short range radiolabeled antibody to the patient and then imaging the breast using conventional radiation imaging techniques to detect the presence of the radiolabel and, therefore, a concentration of a chemokine of the present invention, within the breast. Similarly, by imaging other portions of the patient's body (e.g., lymph nodes), the method can be used to determine whether breast disease (e.g., breast cancer) has spread to other tissues of the body.

Alternatively, the contacting step can be carried out in vitro. For example, the tissue or fluid sample can be a tissue specimen (e.g., cells or tissue sections, preferably preserved by freezing or embedding in paraffin, from the breast, lymph nodes, bone marrow, or other sites of disease dissemination). Alternatively, the tissue or fluid sample can be a fluid specimen (e.g., urine, serum, lymph fluid, and anticoagulated whole blood cells) removed from the patient.

The antibodies and binding portions thereof of the present invention can also be used to treat breast disease, for example, by ablating or killing diseased breast tissue cells. The process involves providing an antibody or binding portions thereof which recognizes a chemokine of the present invention. The antibody or binding portions thereof can be used alone or can be bound to a substance effective to kill cells that are in proximity to an elevated level of a chemokine of the present invention or that bound to the chemokine. In this method, these antibodies or binding portions thereof are contacted with the cells under conditions effective to permit killing or ablating of the cells. In its preferred form, such contacting is carried out in a living patient by administering (e.g., orally or parenterally) the antibody or binding portion thereof to the patient under conditions effective to permit localization of the antibody or binding portion thereof to tissues having elevated concentrations of the subject chemokine and killing or ablating of cells within such tissues.

Antibodies and binding portions thereof suitable for either killing, ablating, or detecting diseased breast tissue cells include antibodies, such as monoclonal or polyclonal antibodies. In addition, antibody fragments, half-antibodies, hybrid derivatives, and other molecular constructs may be utilized. These antibodies and binding portions recognize and bind to chemokines of the present invention, which are associated with breast disease.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (see Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 µl per site at six different sites. Each injected material will contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed in E. Harlow, et. al., editors, *Antibodies: A Laboratory Manual* (1988), which is hereby incorporated by reference.

In addition to utilizing whole antibodies, the processes of the present invention encompass use of binding portions of such antibodies. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, pp. 98–118, New York:Academic Press (1983), which is hereby incorporated by reference.

It is particularly preferred to use antibodies which recognize a chemokine having an amino acid sequence corresponding to SEQ ID NO:1 or a peptide having an amino acid sequence corresponding to SEQ ID NO:3, SEQ ID NO:4, or SEQ ID NO:5. These antibodies can be used alone or as a component in a mixture with other antibodies or other biological agents to treat or image tissues containing a mammary associated chemokine of the present invention.

Regardless of whether the antibodies or binding portions thereof are used for treatment or in vivo detection, they can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. They may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The antibody or binding portion thereof of the present invention may also be administered in injectable dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the antibody or binding portion thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

As indicated above, the antibody or binding portion thereof may be used to detect, in vivo, breast disease in a patient. This is preferably achieved by labeling the antibody or binding portion thereof, administering the labeled antibody or binding portion thereof to the patient, and then imaging the patient.

Examples of labels useful for diagnostic imaging in accordance with the present invention are radiolabels such as $^{131}$I, $^{111}$In, $^{123}$I, $^{99}$mTc, $^{32}$P, $^{125}$I, $^3$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed. The antibody or binding portion thereof can be labeled with such reagents using techniques known in the art. For example, see Wensel and Meares, *Radioimmunoimaging and Radioimmunotherapy*, New York:Elsevier (1983), which is hereby incorporated by reference, for techniques relating to the radiolabeling of antibodies. See also, Colcher et al., "Use of Monoclonal Antibodies as Radiopharmaceuticals for the Localization of Human Carcinoma Xenografts in Athymic Mice", *Meth. Enzymol.* 121:802–816 (1986), which is hereby incorporated by reference.

Detecting the presence of a complex between an antibody or binding portion thereof and a chemokine of the present invention can be carried out by any conventional method for detecting antigen-antibody reactions, examples of which can be found, e.g., in Klein, *Immunology*, New York:John Wiley & Sons, pp. 394–407 (1982), which is hereby incorporated by reference. For in vitro detection of breast disease, the formation of a complex between the antibody and chemokine present in the tissue of fluid sample can be detected by enzyme linked assays, such as ELISA assays. Briefly, the antibody/chemokine complex is contacted with a second antibody which recognizes a portion of the antibody that is complexed with the chemokine. Generally, the second antibody is labeled so that its presence (and, thus, the presence of an antibody/chemokine complex) can be detected. Alternatively, the antibody or binding portion thereof can be bound to a label effective to permit detection of the chemokine upon binding of the antibody or binding portion thereof to the chemokine. Suitable labels include, fluorophores, chromophores, radiolabels, and the like.

For example, a radiolabeled antibody or binding portion thereof of this invention can be used for in vitro diagnostic tests. The specific activity of a tagged antibody or binding portion thereof depends upon the half-life and isotopic purity of the radioactive label and how the label is incorporated into the antibody or its binding portion. Table 1 lists several commonly-used isotopes, their specific activities and half-lives. In immunoassay tests, the higher the specific activity, in general, the better the sensitivity.

TABLE 1

| Isotope | Specific Activity of Pure Isotope (Curies/mole) | Half-Life |
| --- | --- | --- |
| $^{14}C$ | $6.25 \times 10^1$ | 5720 years |
| $^{3}H$ | $2.01 \times 10^4$ | 12.5 years |
| $^{35}S$ | $1.50 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

Procedures for labeling antibodies and binding portions thereof with the radioactive isotopes listed in Table 1 are generally known in the art. Tritium labeling procedures are described in U.S. Pat. No. 4,302,438 to Zech, which is hereby incorporated by reference. Iodinating, tritium labeling, and $^{35}S$ labeling procedures especially adapted for murine monoclonal antibodies are described in Goding, *Monoclonal Antibodies: Principles and Practice*, pp. 124–126, New York:Academic Press (1983) and the references cited therein, which are hereby incorporated by reference. Other procedures for iodinating antibodies or binding portions thereof are described in Hunter et al., *Nature* 144:945 (1962), David et al., *Biochemistry* 13:1014–1021 (1974), U.S. Pat. No. 3,867,517 to Ling, and U.S. Pat. No. 4,376,110 to David et al., which are hereby incorporated by reference. Radiolabeling elements which are useful in imaging include $^{123}I$, $^{131}I$, $^{111}In$, and $^{99m}Tc$, for example. Procedures for iodinating antibodies or binding portions thereof are described in Greenwood et al., *Biochem. J.* 89:114–123 (1963); Marchalonis, *Biochem. J.* 113:299–305 (1969); and Morrison et al., *Immunochemistry* 289–297 (1971), which are hereby incorporated by reference. Procedures for $^{99m}Tc$-labeling are described by Rhodes et al. in Burchiel et al., eds., *Tumor Imaging: The Radioimmunochemical Detection of Cancer*, New York:Masson 111–123 (1982) and the references cited therein, which are hereby incorporated by reference. Procedures suitable for $^{111}In$-labeling antibodies or binding portions thereof are described by Hnatowich et al., *J. Immul. Methods* 65:147–157 (1983), Hnatowich et al., *J. Applied Radiation* 35:554–557 (1984), and Buckley et al., *F.E.B.S.* 166:202–204 (1984), which are hereby incorporated by reference.

The antibodies or binding portions thereof of the present invention can be used and sold together with equipment to detect the particular label as a kit for in vitro detection of breast disease.

In the case of a radiolabeled antibody or binding portion thereof, the antibody or binding portion thereof is administered to the patient, is localized to the region of the patient where diseased breast cells produce increased levels of the subject chemokines, and is detected or "imaged" in vivo using known techniques such as radionuclear scanning using e.g., a gamma camera or emission tomography. See e.g., Bradwell et al., "Developments in Antibody Imaging" in Baldwin et al., eds., *Monoclonal Antibodies for Cancer Detection and Therapy*, pp. 65–85, New York:Academic Press (1985), which is hereby incorporated by reference. Alternatively, a positron emission transaxial tomography scanner, such as the one designated Pet VI located at Brookhaven National Laboratory, can be used where the radiolabel emits positrons (e.g., $^{11}C$, $^{18}F$, $^{15}O$, and $^{13}N$).

Fluorophore and chromophore labeled antibodies and binding portions thereof can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described in Stryer, *Science,* 162:526 (1968) and Brand et al., *Annual Review of Biochemistry,* 41:843–868 (1972), which are hereby incorporated by reference. The antibodies and binding portions thereof can be labeled with fluorescent chromophore groups by conventional procedures such as those disclosed in U.S. Pat. Nos. 3,940,475 to Gross, 4,289,747 to Chu, and 4,376,110 to David et al., which are hereby incorporated by reference.

One group of fluorescers having a number of the desirable properties described above are the xanthene dyes, which include the fluoresceins derived from 3,6-dihydroxy-9-hexylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Antibodies and binding portions thereof can be labeled with fluorchromes or chromophores by the procedures described in Goding, *Monoclonal Antibodies: Principles and Practice*, pp. 208–249, New York:Academic Press (1983), which is hereby incorporated by reference. The antibodies and binding portions thereof can be labeled with an indicating group containing the NMR-active $^{19}$F atom, or a plurality of such atoms inasmuch as (i) substantially all of naturally abundant fluorine atoms are the $^{19}$F isotope and, thus, substantially all fluorine-containing compounds are NMR-active; (ii) many chemically active polyfluorinated compounds such as trifluoroacetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body NMR determination is carried out using an apparatus such as one of those described in Pykett, *Scientific American*, 246:78–88 (1982), which is hereby incorporated by reference, to locate and image regions of elevated chemokine concentration.

The antibodies and binding portions thereof can also be utilized to treat breast disease in vivo. This involves administering to a patient in need of such treatment the antibodies or binding portions thereof by themselves or with a cytotoxic drug to which the antibodies and binding portions thereof are bound. Since the antibodies and binding portions thereof recognize the subject chemokines, diseased breast cells, which are in proximity to elevated levels of the subject chemokines which they produce, are destroyed. Caution must be exercised, however, as such administration may destroy normal cells which are in proximity to the chemokines produced by the diseased breast cells.

The antibodies and binding portions thereof of the present invention may be used to deliver a variety of cytotoxic drugs including therapeutic drugs, a compound emitting radiation, molecules of plants, fungal, or bacterial origin, biological proteins, and mixtures thereof.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, Saponaria officinalis inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the antibodies and binding portions thereof with the cytotoxic agents have been previously described. Procedures for conjugating chlorambucil with antibodies are described in Flechner, *European Journal of Cancer* 9:741–745 (1973); Ghose et al., *British Medical Journal* 3:495–499 (1972); and Szekerke et al., *Neoplasma* 19:211–215 (1972), which are hereby incorporated by reference. Procedures for conjugating daunomycin and adriamycin to antibodies are described in Hurwitz et al., *Cancer Research* 35:1175–1181 (1975) and Arnon et al. *Cancer Surveys* 1:429–449 (1982), which are hereby incorporated by reference. Procedures for preparing antibody-ricin conjugates are described in U.S. Pat. No. 4,414,148 to Jansen et al. and in Osawa et al. *Cancer Surveys* 1:373–388 (1982) and the references cited therein, which are hereby incorporated by reference. Coupling procedures are also described in EP 86309516.2, which is hereby incorporated by reference.

The use of the subject antibodies and binding portions thereof can also be used in a drug/prodrug treatment regimen. In this method, for example, a first antibody or binding portion thereof according to the present invention is conjugated with a prodrug which is activated only when in close proximity with a prodrug activator. The prodrug activator is conjugated with a second antibody or binding portion thereof, preferably one which binds to diseased breast cells or to other biological materials associated with diseased breast cells (e.g., another protein produced by diseased breast cells). Drug-prodrug pairs suitable for use in the practice of the present invention are described in Blakely et al., "ZD2767, an Improved System for Antibody-directed Enzyme Prodrug Therapy That Results in Tumor Regressions in Colorectal Tumor Xenografts," *Cancer Research* 56:3287–3292 (1996), which is hereby incorporated by reference.

Alternatively, the antibody or binding portion thereof can be coupled to high energy radiation emitters, for example, a radioisotope, such as 131I, a γ-emitter, which, when localized at the diseased breast tissue site, results in a killing of several cell diameters. See, e.g., Order, "Analysis, Results, and Future Prospective of the Therapeutic Use of Radiolabeled Antibody in Cancer Therapy" in Baldwin et al., eds., *Monoclonal Antibodies for Cancer Detection and Therapy*, pp 303–316, New York:Academic Press (1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y.

Where the antibodies or binding portions thereof are used alone to treat breast disease, such treatment can be effected by initiating endogenous host immune functions, such as complement-mediated or antibody-dependent cellular cytotoxicity.

The antibodies or binding portions thereof of the present invention can be used in conjunction with other therapeutic treatment modalities. Such other treatments include surgery, radiation, cryosurgery, thermotherapy, hormone treatment, chemotherapy, vaccines, and other immunotherapies.

Also encompassed by the present invention is a method of treating breast disease which involves using the antibodies and binding portions thereof without cytotoxic agents for prophylaxis. For example, the antibodies and binding portions thereof can be used to prevent or delay development or progression of breast disease by binding to the chemokines of the present invention and, thus, inhibiting their biological activity.

Another aspect of the present invention relates to an isolated nucleic acid molecule which encodes a chemokine of the present invention. The encoded chemokine is preferably one that is preferentially expressed in breast tissue or one which can be detected in breast milk. The encoded chemokine can include from about 100 to about 132 amino acids, preferably from about 105 to about 127 amino acids, more preferably, about 105 or 127 amino acids; can have a deduced molecular weight of from about 10 to about 16 kDa, preferably from about 12 kDa to about 14 kDa; and can have a deduced isoionic point of from about pH 10.1 to about pH 10.7, preferably about 10.4. The term "isolated nucleic acid molecules" is intended to refer to nucleic acid molecules that are substantially free of the biological materials with which they are naturally found. The term "nucleic acid" is meant to refer to polydeoxyribonucleotides ("DNA"), which contain 2-deoxy-D-ribose, to polyribonucleotides ("RNA"), which contain D-ribose, and to any other type of polynucleotide which is an N-glycoside of a purine or pyrimidine base or a modified purine or pyrimidine base. The term "nucleic acid" refers only to the primary structure of the molecule, and, thus, it is meant to include double- and single-stranded DNA as well as double- and single-stranded RNA. There is no intended distinction in length between the terms "nucleic acid" and "oligonucleotide", and these terms are used interchangeably herein.

The nucleic acid molecule can be a DNA or RNA molecule which encodes a chemokine having an amino acid sequence corresponding to SEQ ID NO:1. One such nucleic acid molecule has a nucleotide sequence corresponding to SEQ ID NO:6 as follows:

```
AACATCCTCA CTTGTGTTGC TGTCAGTGCC TGTANGGCAG

GCAGGAATGC AGCAGAGAGG ACTCGCCATC GTGGCCTTGG

CTGTCTGTGC GGCCCTACAT GCCTCAGAAG CCATACTTCC

CATTGCCTCC AGCTGTTGCA CGGAGGTTTC ACATCATATT

TCCAGAAGGC TCCTGGAAAG AGTGAATATG TGTCGCATCC

AGAGAGCTGA TGGGGATTGT GACTTGGCTG CTGTCATCCT

TCATGTCAAG CGCNGAAGAA TCTGTGTCAG CCCGCACAAC

CATACTGTTA AGCAGTGGAT GAAAGTGCAA GCTGCCAANA

AAAATGGTAA AGGAAATGTT TGCCACAGGA AGAAACACCA

TGGCAAGAGG AACAGTAACA GGGCACATCA GGGGAAACAC

GAAACATACG GCCATAAAAC TCCTTATTAG AGAATCTACA

GATAAATCTA CAGAGACAAT CCCCCAAGTG GACTTGGCCA

TGATTGGTTG TAAGTTTATC ATCTGAATTC TCCTTATTGT

AGACAACAGA ACAAAACAAA ATATTGGTTT TTAAAAAATG

AACAATTGTG CCGTATGCAA ATGTACCCAA TAATATACTC

CACTGGAAAA TGAAATGAAA AAANNATACT GGCTGGGTAT

GGTGGGTCCC CCCTTTTATC CCANNNNCTT CGGGAGGCAG

AGGCAGGAGG ATCACTTGAG ACCAGGANTT NGAGACNAGC

TNGGGGCAAA ANAGCAANGA CNTCATTTNT ACAAACNAAA

AAAAANNTTG GCCCGGCNTG GTAGNACTTG CNTATAATCC

CAGCNACATG GGAGGTNGAG GTGGGAGGAT CACTTGAGTC

TGGGNGAGTT NGAGGTNGCA GTGAGCAGCN TGGGTGACAG

AATGNAGACC NTGTCTCTAA AAATAATAAT AATAATGATA

GTGTATATCT TCATATAATA TTTTAAGNAG GAGCATATAG

ATATAACTTN CTCCCAACTT TTTAATTATA GTTTTCCAAA

CTTACAGAGA AGTTAAAAGA ATGGTACAAT GAACATCTAT

ATATCTTTCA CCACAATATT AATCATTGTT AATATTGTGC

CACATTTGCT TTCTCTCTCC TCTCTTGGTA GGGGTTNCAA

TATAAAATAT TATAACTTTT AAAATATATC TTGTTTTGCT

AACCATTGGA AAATAAGTTG CAAAAATCAT GACACTTCAC

CCCTAGTTTC TTTTNGGTGT TATAACTTGA CATACCCTAA

AATAAAGACA TTTTTCTACA TAATCACCTT ATCAGTTTTA
```

-continued

```
TACCTAAAAA ATTAATAATT TCATCTAATA TATTCCATAT

TCAAATTTTC CCAACTATTT AGAGAGCATT TTATGTAGTT

TTTTTTTCAC TCCAGTAATC AATCAAGGTN GACATACATA

TTGCAAATAA TTGTTATTTT TCTTTAATAT CTTTCAATCT

AAGAAAGTTC CTCTGTCTTT TTTTTTTAAT TTTTAAAATT

ATTTTGTTGA GGGAGGGTCT TGCTGTGTCT TCCAGGCTGG

AGTGCAGTGG CACAATTTTG ATTTTGGCTC ACTGAAGCCT

CAACTTTAGG GCTCAAGCAA TCCTCCCACC TCAGCCTNCC

CGAGTATCTG GGATCAAGGT GCATACCCAC CACACCTGGC

TAATTTTGTT TATTTTTTGT AGAGACAGGG TCTCACTATG

TTGCCCAGGT TGATCTCAAA CTCCTGGGCT CAAGCGATCC

TCCCACCTTA GCCTCCCAAA GTACTGGGAT TATAGGTGTG

AGCCACAGTG CCTGGCCTAA TTATTTTCTT GTGATCAAAT

TCAGGTTTAA TGTTTTTGGT TAAGAATTTC CTACGTGAAT

TCGTGTACTT ATTTTGTCAT TTAGAGTTCA TAAATATTAG

GGTTTATTTT CTAAATAGAA TAGTTTAAAC TAAATATAAC

TTCAAAACGT CTAGTTTGAG TAGCTACCGT TGTTTGGATT

GAAATTTTCT GATACTGAAA AGAACAAAAA GCCTGCCTTT

CTGCCCANAA CSNNTTGCYT CCCCCAGTNA GTTCTTGGNG

CAGNACTAGT TAGGGNCCCA GAGTTNGGCC TTNNGKGTGG

TGATTTTANG YTCTGCCTAA ACAAGGNGCN WACATYTTTT

AGCTCCTATT CCACCYTTCT NAMAMGTTTT TGTTGTKGTT

TGNTTGTTTT TTTKGAGACA GRRTNTNAYT CTGTTTGCCC

ARGCTGGART TGCAGTGGCA CAATYTNGGY TNCATTGCAA

CYTCNGCYTC CSSGCCGTTC AAKTGATYYT CTTGCYTCAG

CYTCCCCAAG TAANTGATAT TACAGGNGCC CAGCCACCAM

ACCCCGNTGA WTTTTGTATT TTTARTARAR AMRGGGTTTT

CCCGCNTTGG CNGGGCTGGT CTCNAANTCC TTGAMCTCNA

KTGAACCACC CGCCTGTGCC YCCCAAANTG CTGGAATTAC

CANCGTTGAN CCACCATGCC GGGCYCACAC GTTTGARTTT

GANACCATTG TNCCATTCCT CTTTTGGCCT YTTTTTTNTC

CATAGNNGCT TCAAGATAGA TANGTAAGRG CCCAGTAGTN

GTTCWTARGA AGCNMATAGR RANCRGGARC CANTTTNATC

AGGTGGGCAG GTGTCCNNGG CYTCCCTGCT GGYTNNTCCC

AAGCGGTGGT GTTGCCARGA NKTNTTGGAR GTGATAATGG

GANANACCAG NAGGCMCTGA GTYNCNNTAG GTTNAAATGC

CACCAAAACT GGCCTTTGGC CTAATATCCY YCNTTGAMTA

NTTARCATTT AWTTTATTWA TTTNCCTGAC ATTTNTGCMA

NCCTTTGTWT TTNTATTTCC NCTNTATARA WGARGAAATT

TGAGGNTYTT ARAGGTAAAA TGANTTGCNC NRGTNNACMC
```

```
                        -continued
AGGAAGTGGC NRARANAANC TTTTTANATN MGAAAAAATT

AATAAAATAT AATATGAGAG TAACTTAAAA TATTAATAAA

CCACAATTTT AAATTAATTA ACCGTGATAA CCAACATTAA

TAAAAGTTAA GATACCAAAA CACTGGTGTN TAATTTTTTN

AACTAACAAN TTGAATTATT TTCCATTTTA AATTAATTAA

CCGTGATAAC CAACATTAAT AAAAGTTAAG ATACCGN
```

Another such nucleic acid molecule has a nucleotide sequence corresponding ti SEQ ID NO:7 as follows:

```
ATGCAGCAGA GAGGACTCGC CATCGTGGCC TTGGCTGTCT

GTGCGGCCCT ACATGCCTCA GAAGCCATAC TTCCCATTGC

CTCCAGCTGT TGCACGGAGG TTTCACATCA TATTTCCAGA

AGGCTCCTGG AAAGAGTGAA TATGTGTCGC ATCCAGAGAG

CTGATGGGGA TTGTGACTTG GCTGCTGTCA TCCTTCATGT

CAAGCGCNGA AGAATCTGTG TCAGCCCGCA CAACCATACT

GTTAAGCAGT GGATGAAAGT GCAAGCTGCC AANAAAAATG

GTAAAGGAAA TGTTTGCCAC AGGAAGAAAC ACCATGGCAA

GAGGAACAGT AACAGGGCAC ATCAGGGGAA ACACGAAACA

TACGGCCATA AAACTCCTTA T
```

This nucleic acid represents an open reading frame of the nucleic acid molecule having a nucleotide sequence corresponding to SEQ ID NO:6.

The isolated nucleic acid molecules of the present invention which encode for chemokines of the present invention can be used along with conventional recombinant methods to produce isolated chemokines of the present invention Briefly, this is carried out by incorporating any one of the DNA molecules encoking chemokines of the present invention in cells using conventional recombinant DNA technology. This involves inserting the selected DNA molocule into an expression system to which that DNA molecule is heterologous (i.e., not normally present). The heterologous DNA molecule is inserted into the expression system or vector in proper orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids are then introduced by means of transformation and replaced in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vector such as pBR322, pBR325, pACYC177, pACYC184, pUC8, pUC9, pUC18, pUC19, pLG339, pR290, pKC37, pKC101, SV 40, pBluescript II SK+/- or KS+/- (see "Stratagene Cloning Systems" Catalog (1993) from Stratagene, La Jolla, Calif., which is hereby incorporated by reference), pQE, pIH821pGEX, pET series (see Studier et. al. "Use of T7 RNA Polymerase to Direct Expression of Cloned Genes" in *Gene Expression Technology*, vol. 185 (1990), which is hereby incorporated by reference) and any derivatives thereof. Recombinant molecules can be introduced into cells via transformation, particularly transduction, conjugation, mobilization, or electroproation. The DNA sequences are cloned into the vector using standard cloning procedures in the art, as described by Maniatis et al., *Molecular Cloning: A Laboratory Manual*, Cold Spring Harbor, N.Y.: Cold Springs Laboratory Press (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eucaryotic promotes differ from those of procaryotic promoters. Furthermore, eucaryotic promoters and accompanying genetic signals may not be recognized in or may not function in a procaryotic system, and, further, procaryotic promoters are not recognized and do not function in eucaryotic cells Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts et al., *Methods in Enzymology* 68:473 (1979), which is hereby incorporated by reference.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in E. coli requires a Shine-Dalgarno ("SD") sequence about 7–9 bases 5' to the initiation codon (ATG) to provide a ribosome binding site. Thus, any SD-ATG combination that can be utilized by host cell ribosomes may be employed. Additionally, any SD-ATG combination produced by recombinant DNA or other techniques involving incorporation of synthetic nucleotides may be used.

Once the desired isolated DNA molecule encoding a chemokine according to the present invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

Recombinant DNA technology can also be used to produce fragments of the above chemokines, such as the above-referenced peptides. For example, subclones of the gene encoding a subject chemokine are produced by conventional molecular genetic manipulation by subcloning gene fragments. The subclones then are expressed in vitro or in vivo in bacterial cells to yield a smaller peptide that can be tested for its antigenic activity (i.e., capacity to be used as an antigen to raise antibodies which recognize an antigenic portion of the chemokine).

As an alternative, protein fragments can be produced by digestion of a full-length subject chemokine with proteolytic enzymes like chymotrypsin, Staphylococcus proteinase A, or trypsin. Different proteolytic enzymes are likely to cleave proteins at different sites based on the amino acid sequence of the protein. Some of the fragments that result from proteolysis may have antigenic activity.

In still another approach, based on knowledge of the primary structure of the subject chemokines, fragments of the encoding gene may be synthesized by using the polymerase chain reaction ("PCR") technique together with specific sets of primers chosen to represent particular portions of the protein. These then would be cloned into an appropriate vector to facilitate expression of a peptide having, for example, antigenic activity.

Chemical synthesis can also be used to make suitable fragments. Such a synthesis is carried out using known amino acid sequences for the chemokines of the present invention. Alternatively, subjecting a full length subject chemokine to high temperatures and pressures will produce fragments. These fragments can then be separated by conventional procedures (e.g., chromatography and SDS-PAGE).

The chemokines of the present invention and their fragments can optionally be modified by, for example, the deletion or addition of amino acids that have minimal influence on the properties, secondary structure, and hydropathic nature of the chemokine or fragments. For example, a chemokine or peptide of the present invention can be conjugated to a signal (or leader) sequence at the N-terminal end of the chemokine which co-translationally or post-translationally directs transfer of the protein. The chemokine or peptide can also be conjugated to a linker or other sequence for ease of protein synthesis, purification, or identification. The peptides of the present invention can also include, in addition to the antigenic portion of the chemokine, other amino acid sequences, such as T-cell antigenic stimuli and other amino acid sequences which increase the peptide's immunogenicity.

As indicated above, the chemokines and peptides of the present invention are preferably produced in purified form (preferably at least about 80%, more preferably 90% pure) by conventional techniques. The chemokines or peptides of the present invention are preferably produced in purified form by conventional techniques, of which the following is one example. To isolate the proteins, an E. coli host cell carrying a recombinant plasmid is propagated and homogenized, and the homogenate is centrifuged to remove bacterial debris. The supernatant is then subjected to sequential ammonium sulfate precipitation. The fraction containing the chemokines or peptides of the present invention is subjected to gel filtration in an appropriately sized dextran or polyacrylamide column to separate the chemokines or peptides. If necessary, the chemokine or peptide fraction may be further purified by ion exchange chromatography and/or HPLC.

As indicated above, the chemokines and peptides of the present invention can be used to raise antibodies which are useful in the detection and treatment of breast disease. Breast disease can also be treated using the peptides of the present invention by administering to a patient suffering from breast disease an effective amount of a peptide which binds to a cellular receptor for a chemokine of the present invention. Methods for identifying peptides which bind to cellular receptors of proteins having known amino acid sequences are well known to those skilled in the art and are described in, for example, Wells et al., "Selectivity and Antagonism of Chemokine Receptors," *J. Leukocyte Biol.*, 59:53–60 (1996) and Horuk, "Molecular Properties of the Chemokine Receptor Family," *Trends Pharmacol. Sci.*, 15:159–165 (1994), which are hereby incorporated by reference.

The present invention also relates to isolated nucleic acid molecules which, under stringent conditions, hybridize to a nucleic acid molecule encoding a chemokine of the present invention. Such isolated nucleic acid molecules include those which hybridize, under stringent hybridization conditions, to nucleic acid molecules (1) which encode chemokines that are preferentially expressed in breast tissue or that are detected in breast milk; (2) which encode chemokines which include from about 100 to about 132 amino acids, which have a deduced molecular weight of from about 10 to about 16 kDa, and which have a deduced isoionic point of from about pH 10.1 to about pH 10.7; (3) which encode chemokines which include from about 105 to about 127 amino acids, which have a deduced molecular weight of from about 12 to about 14 kDa, and which have an isoionic point of about pH 10.4; (4) which encode chemokines having an amino acid sequence corresponding to SEQ ID NO:1; (5) which have a nucleotide sequence corresponding to SEQ ID NO:6; and (6) which have a nucleotide sequence corresponding to SEQ ID NO:7. Preferably, the nucleic acid molecules which hybridize under stringent conditions to nucleic acid molecules encoding a chemokine of the present invention preferentially hybridize to nucleic acid molecules from breast tissue. That is, more of the chemokine of the present invention will hybridize, under stringent conditions, to nucleic acid molecules from breast tissue that to nucleic acid molecules from other tissues in the body.

The present invention also relates to isolated nucleic acid molecules which, under stringent conditions, hybridize to the complement of a nucleic acid molecule encoding a chemokine of the present invention.

"Stringent conditions", as used herein in relation to hybridization, mean approximately 35° C. to 70° C., preferably about 50° C., 55° C., 60° C., and/or 65° C., in a salt solution of approximately 0.9 molar NaCl. These conditions are frequently represented by a wash stringency of 0.3 M NaCl, 0.03 M sodium citrate, 0.1% SDS at 70° C. to a DNA molecule encoding a chemokine of the present invention in a standard in situ hybridization assay. See Sambrook et al., *Molecular Cloning: A Laboratory Manual*, 2nd ed., Cold Spring Harbor, N.Y.:Cold Spring Harbor Laboratory (1989). In general, such sequences will be at least 95% homologous, often at least 98% homologous, and even at least 99% homologous with the sequences of DNA molecules encoding chemokines of the present invention.

Illustrative nucleic acid molecules include those which have a nucleotide sequence corresponding to ACACGAATTCACGTAGGAAATTCTTAACCAAAAACA
TTAAACCTGAATTTGATCACAA-
GAAAATAATTAGGCCAGGCACTGTGGCTCA CAC-
CTATAATCCCAGT (SEQ ID NO:8),

GAATTCACGTAGGAA ATTCTTAACC (SEQ ID NO:9),

ACTGGGATTATAGGTGTGAGCC (SEQ ID NO:10), and

GGAGAGAGCCGTATGTTTCGTGTTTC-
CCCTGATGTGCCCTGTTACTGTTCCTCT TGCCATGGT-
GTTTCTTCCTGTGGCAAACATTTCCTT-
TACCATTTTNTTGGCAG
CTTGCACTTTCATCCACTGCTTAACAG-
TATGGTTGTGCGGGCTGACACAGATT NTTCTGCGCT-
TGACATGAAGGATGACAGCAGCCAAGT-
CACAATCCCCATCAG
CTCTCTGGATGCGACACATAT-
TCACTCTTTCCAGGAGCCTTCTGGAAATATGA TGT-
GAAACCTCCGTGCAACAGCTGGAG-
GCAATGGGAAGTATGGCT (SEQ ID NO:11), as well as to those which have a nucleotide sequence corresponding to a complement of and of SEQ ID NOs:.8–11. Of course, as one skilled in the art will recognize, although these exemplary nucleic acid molecules have a defined number of nucleotides, one or more nucleotides may be added or deleted from a particular nucleic acid molecule without great impact on its ability to hybridize with a nucleic acid molecule encoding a chemokine of the present invention.

The exact size of nucleic acid molecules which hybridize under stringent conditions to nucleic acid molecules encoding a chemokine of the present invention depends on many factors and the ultimate use to which the nucleic acid molecule is to be put. These nucleic acid molecules can be prepared by any suitable method, such as by cloning and restriction of appropriate sequences and by direct chemical synthesis using, for example, the phosphotriester method (described in, e.g., Narang et al., *Meth. Enzymol.* 68:90–99 (1979), which is hereby incorporated by reference); the phosphodiester method (described in, e.g., Brown et al., *Meth. Enzymol.* 68:109–151 (1979), which is hereby incorporated by reference); the diethylphosphoramidite method (described in, e.g., Beaucage et al., *Tetrahedron Lett.* 22:1859–1862 (1981), which is hereby incorporated by reference); and the solid support method (described in, e.g., U.S. Pat. No. 4,458,066 to Caruthers et al., which is hereby incorporated by reference). These and other methods for synthesizing oligonucleotides are described in Goodchild, *Bioconjugate Chemistry* 1(3):165–187 (1990), which is hereby incorporated by reference.

The nucleic acid molecules which hybridize under stringent conditions to nucleic acid molecules encoding a chemokine of the present invention can be used as probes in hybridization assays to detect breast disease in a patient. For example, a sample of tissue or body fluid from the patient is contacted with a nucleic acid probe which, under stringent conditions, hybridizes to a nucleic acid molecule encoding a chemokine according to the present invention or to a complement thereof. The contacting is carried out under conditions effective to permit formation of a hybridization complex between the probe and breast tissue specific nucleic acid molecules (i.e., the nucleic acid molecules encoding chemokines of the present invention). Breast disease is then detected by detecting the hybridization complex.

As used herein, the term "probe" refers to an oligonucleotide which forms a duplex structure with a sequence of a target nucleic acid (e.g., a nucleic acid molecule which encodes a chemokine of the present invention) due to complementary base pairing. The probe will contain a hybridizing region, which is a region of the oligonucleotide corresponding to a region of the target sequence. A probe oligonucleotide either can consist entirely of the hybridizing region or can contain additional features which allow for the detection or immobilization of the probe but do not alter the hybridization characteristics of the hybridizing region. The term "probe" also refers to a set of oligonucleotides which provide sufficient sequence variants of the hybridization region to permit hybridization with each member of a given set of target sequence variants. Additionally, a probe can contain mismatches with some or all members of a given set of target sequence variants, provided that it contains sufficient regions of complementarity with each target sequence variant to permit hybridization with all target sequence variants under suitable conditions.

Samples of the patient's tissue or body fluids suitable for the use in the detection method using probes include those which are discussed above with regard to detection methods employing antibodies.

Detection of the hybridization complex can be carried out by a variety of conventional methods. These include electrophoresis, DNA sequencing, blotting, microplate hybridization, or microscopic visualization. Alternatively, the probe can have bound thereto a label, such as detectable functional nucleotide sequence (e.g., a T7 site, a restriction site, and the like) or one of the labels described above as suitable for use in the detection method of the present invention employing antibodies. Detection, in this case, involves detecting the presence of the label, for example using the techniques discussed above or by using one of the conventional methods for detecting detectable functional nucleotide sequences.

The nucleic acid molecules which hybridize under stringent conditions to nucleic acid molecules encoding a chemokine of the present invention can also be used as primers in a DNA amplification assay to detect breast disease in a patient. For example, a sample of tissue or body fluid from the patient can be contacted with a nucleic acid primer which, under stringent conditions, hybridizes to a nucleic acid molecule encoding a chemokine according the present invention or to a complement thereof. The sample of tissue or body fluid from the patient in contact with the nucleic acid primer is then treated under conditions effective to amplify breast tissue specific nucleic acid molecules, and the breast tissue specific nucleic acid molecules, thus amplified, are then detected.

As used herein, the term "primer" refers to an oligonucleotide, whether natural or synthetic, capable of acting as a point of initiation of a DNA synthesis under conditions which produce a primer extension product complementary to a nucleic acid strand is induced. Generally, the DNA synthesis is carried out in the presence of four different nucleoside triphosphates and an agent for polymerization (e,g., DNA polymerase or reverse transcriptase) in an appropriate buffer (e.g., Tris-HCl), and at suitable temperatures (e.g., at an annealing temperature of from about 45 to about 85° C.; at an extending temperature of from about 55 to about 75° C.; and at a melting temperature of about 95° C.). The primer is preferably a single-stranded DNA. The optimal length of the primer depends on the primer's intended use but typically ranges from 15 to 35 nucleotides. Short primer molecules generally require cooler temperatures to form sufficiently stable hybrid complexes with the template. A primer need not complement the exact sequence of the template but must be sufficiently complementary to hybridize with a template. Primers can incorporate additional features which allow for the detection or immobilization of the primer but do not alter the basic property of the primer, that of acting as a point of initiation of DNA synthesis. The term "primer", as used herein, also refers to a set of oligonucleotides which provide sufficient sequence variants of the hybridization region to permit hybridization with each member of a given set of target sequence variants, so as to act as a point of initiation of DNA synthesis. Additionally, a primer may consist of one or more oligonucleotides which contain mismatches with some or all members of a given set of target sequence variants, but contains sufficient regions of complementarity with each target sequence variant so as to enable hybridization with all target sequence variants under suitable conditions. The term "consensus primers" is used herein to refer to primers containing a single oligonucleotide complementary to a consensus target sequence, to primers consisting of multiple oligonucleotides complementary to a consensus target sequence, and to combinations thereof.

Samples of the patient's tissue or body fluids suitable for the use in the detection method using probes include those which are discussed above with regard to detection methods employing antibodies.

Amplification of breast tissue specific nucleic acid molecules (i.e., nucleic acid molecules encoding the chemokines of the present invention) is preferably carried out by PCR. Use of PCR to amplify DNA is described in U.S. Pat. No. 4,683,195 to Mullis et al., U.S. Pat. No. 4,683,202 to Mullis, and U.S. Pat. No. 4,965,188 to Mullis et al., which are hereby incorporated by reference. Briefly, PCR amplification of DNA involves repeatedly heat-denaturing the DNA, annealing two oligonucleotide primers to sequences that flank the DNA segment to be amplified, and extending the annealed primers with DNA polymerase. The primers hybridize to opposite strands of the target sequence and are oriented so DNA synthesis by the DNA polymerase proceeds across the region between the primers, effectively doubling the length of that DNA segment. Moreover, because the extension products are also complementary to and capable of binding primers, each successive cycle essentially doubles the amount of DNA synthesized in the previous cycle. This results in the exponential accumulation of the specific target fragment at a rate of approximately $2^n$, where n is the number of cycles. Due to the enormous amplification possible with the PCR process, small levels of DNA carryover from samples with high DNA levels can result in PCR product, even in the absence of purposefully added template DNA. Optimally, all reaction mixes are set up in an area separate from PCR product analysis and sample preparation and care is taken to avoid cross contamination, for example, by using dedicated or disposable vessels, solutions, pipettes (preferably positive displacement pipettes), and pipette tips (preferably with aerosol barriers) for RNA/DNA, reaction mixing, and sample analysis. See e.g., Higuchi et al., *Nature* 339:237–238 (1989) and Kwok et al. in Innis et al., eds., *PCR Protocols: A Guide to Methods and Applications*, San Diego, Calif. Academic Press, Inc., pp. 142–145 (1990), which are incorporated herein by reference.

Primers suitable for use in the method of the present invention are preferably 15 to 30 nucleotides in length and are designed to have a high degree of homology with breast tissue specific nucleic acid sequences (i.e., with nucleic acid molecules encoding chemokines of the present invention). For each region to be amplified, two regions of homology are required, one for negative-strand primers and another for positive-strand primers. Once a homologous region is identified, a consensus primer is designed. Degenerate bases can be used in the design to accommodate positions at which an individual breast tissue gene varies in sequence from the consensus sequence (genetic polymorhpism). Preferably, as many degenerate positions are made as is necessary so that all breast tissue sequences have fewer than three mismatches with the consensus primer. Any mismatches that are not accommodated by the degenerate positions in the primer should preferably be located more than 3 bases from the 3' end of the primer. Likewise, any degenerate positions should preferably be more than 3 bases from the 3' end of the primer. Degenerate primers having estimated minimum and maximum Tms of about 54° C. and about 64° C., respectively, are preferred, where Tms are estimated by summing a contribution from each base pair. In this formulation, each G or C contributes 4° C. to the Tm, and each A or T contributes 2° C. to the Tm. Finally, it is generally preferred that primers be designed so that they do not span palindromes or repetitive sequences.

Following amplification, the breast tissue specific nucleic acid molecules are detected to determine whether amplification has occurred. Since amplification will occur (and breast tissue specific nucleic acid molecules will be detected) only if some amount of breast tissue specific nucleic acid molecules were present in the sample before amplification, detection of breast tissue specific nucleic acid molecules after amplification indicates the presence of breast disease in the patient from which the sample came.

Suitable nucleic acid primers include those which, under stringent hybridization conditions, hybridize to a nucleic acid molecule encoding a chemokine having an amino acid sequence corresponding to SEQ ID NO:1 and/or which hybridize to a nucleic acid molecule having a nucleotide sequence corresponding to SEQ ID NOs:.6–8. In particular, suitable nucleic acid primers include those having a nucleotide sequence corresponding to SEQ ID NO:9 or SEQ ID NO:10.

There are a variety of known methods for determining whether amplification has occurred. For example, a portion of the PCR reaction mixture can be subjected to gel electrophoresis, the resulting gel can be stained with, for example, a ultraviolet absorbing stain, such as with ethidium bromide, and the stained gel can be exposed to ultraviolet light to determine whether a product of the expected size can be observed. Alternatively, labeled PCR primers or labeled deoxyribonucleoside 5'-triphosphates can be used to incorporation the label into the amplified DNA. The presence of a breast tissue specific nucleic acid amplification product can then be detected by detecting the label. Examples of suitable labels and label detection methods include those set forth above with regard to the detection method which employed hybridization. Another method for determining if amplification has occurred involves testing a portion of the amplified reaction mixture for ability to hybridize to a labeled probe designed to hybridize only to the amplified DNA. Amplified breast tissue specific nucleic acid molecules can also be detected by DNA sequencing as well as by microscopic visualization.

A number of treatments can be used to amplify the breast tissue specific nucleic acid molecules (i.e., nucleic acid molecules encoding a chemokine of the present invention). These include PCR, ligase chain reaction ("LCR"), self-sustained sequence ("3SR") replication, Q-beta replicase, nucleic acid sequence based amplification ("NASBA"), transcription-based amplification System ("TAS"), or branched-DNA methods.

Although PCR is the preferred amplification method, amplification of target sequences in a sample may be accomplished by any known amplification method, such as ligase chain reaction methods (described, e.g., in Wu et al., *Genomics* 4:560–569 (1988), which is hereby incorporated by reference). In LCR, the consensus primers can be used to direct the joining of oligonucleotide segments that anneal to the target nucleic acid, thereby amplifying the target. Further details with regard to this method can be found in, for example, WO 89/09835, which is hereby incorporated by reference. Other suitable amplification methods include the TAS amplification system (described, e.g., in Kwoh et al., *Proc. Natl. Acad. Sci. USA* 86:1173–1177 (1989), which is hereby incorporated by reference), branched-DNA methods (described, e.g., in Kern et al., *J. Clin. Microbiol.* 34:3196–3202 (1996), which is hereby incorporated by reference), and self-sustained sequence replication methods (described, e.g., in Guatelli et al., *Proc. Natl. Acad. Sci. USA* 87:1874–1878 (1990), which is hereby incorporated by reference). Each of these methods provides sufficient amplification so that the target sequence can be detected by nucleic acid hybridization to an oligonucleotide probe, such as those described above, or by other detection methods. Alternatively, methods that amplify the probe to detectable levels, such as Q-beta replicase amplification can be employed. This method is described in, for example, Kramer et al., *Nature* 339:401–402 (1989) and Lomeli et al., *Clin. Chem.* 35:1826–1831 (1989), which are hereby incorporated by reference. Further details regarding these and other suitable amplification methods are provided in Abramson et al., *Current Opinion in Biotechnology* 4:41–47 (1993), which is hereby incorporated by reference. The term "probe", as used with regard to the above amplification methods, encompasses any of the sequence-specific oligonucleotides used in these procedures. For instance, the two or more oligonucleotides used in LCR are "probes" for purposes of the present invention, even though some embodiments of LCR only require ligation of the probes to indicate the presence of an allele.

In some cases, the tissue or fluid sample from the patient may contain a breast tissue specific nucleic acid transcript (i.e., mRNA) which codes for the chemokine of the present invention. In this situation, the mRNA can be converted to cDNA by reverse transcription-PCR ("RT-PCR") prior to amplification. This involves treating the mRNA-containing sample with reverse transcriptase in an appropriate reaction mixture and in the presence of an appropriate primer. The primer used in the reverse transcription reaction can be a consensus primer of the present invention, or it can be a different oligonucleotide that hybridizes near the 3' end of the mRNA. Although random hexamers are not specific for the 3' end of the mRNA molecule, they are suitable for reverse transcription of mRNA to provide a cDNA template for amplifying breast tissue specific nucleic acids. This cDNA copy is then made into a double stranded DNA molecule, which can be amplified as described above.

The nucleic acid primer used in the above amplification detection method may be assembled as a kit for detecting breast disease. Such a kit includes consensus primers and molecular probes. A preferred kit also includes the components necessary to determine if amplification has occurred. The kit may also include, for example, PCR buffers and enzymes; positive control human breast tissue specific sequences, reaction control primers, such as betaglobin primers; and instructions for amplifying and detecting breast tissue specific sequences.

The symbols used herein to designate particular nucleotides are set forth below in Table 2.

TABLE 2

| Symbol | Meaning |
|--------|---------|
| G | guanine |
| A | adenine |
| T | thymine |
| C | cytosine |
| R | adenine or guanine |
| Y | cytosine or thymine |
| M | adenine or cytosine |
| K | guanine or thymine |
| S | cytosine or guanine |
| W | adenine or thymine |
| H | adenine or cytosine or thymine |
| B | cytosine or guanine or thymine |
| V | adenine or cytosine or guanine |
| D | adenine or guanine or thymine |
| N | adenine or cytosine or guanine or thymine |

The present invention is further illustrated by the following examples.

EXAMPLES

Example 1

Isolation of Novel Human Breast Tissue Specific Nucleic Acid Sequences Using Suppression Subtractive Hybridization Suppression Subtractive Hybridization ("SSH") was performed according to the protocol of Diatchenko et al., *Proc. Natl. Acad. Sci. USA* 93:6025–6030 (1996), which is hereby incorporated by reference, using commercial reagents from Clontech (PCR-Select cDNA subtraction kit). Human polyA RNAs derived from bone marrow, skeletal muscle, lung, liver, pancreas, and mammary gland were obtained from Clontech, and 2 mg of each were reverse transcribed. The cDNAs derived from mammary gland were subdivided and ligated to different cDNA adaptors according to the manufacturer's protocol. Primary and secondary subtractive hybridizations were performed by adding an excess of denatured cDNAs derived from human bone marrow, lung, pancreas, liver, and skeletal muscle ("driver" cDNAs") to the mammary gland cDNA ("tester cDNA"). The entire population of subtracted molecules was subjected to two rounds of DNA amplification: a primary PCR to amplify differentially expressed sequences and a secondary (nested) PCR to enrich for those sequences. PCR primers 1 and 2 and nested PCR primers 1 and 2 (Clontech) were used in accordance with the protocol of the PCR-Select cDNA subtraction kit for primary and secondary PCR, respectively. All DNA amplifications were performed with a Perkin-Elmer DNA Thermal Cycler Model 2400 using parameters of 94° C., 5 seconds (denature); 68° C., 30 seconds (anneal); and 72° C., 150 seconds (extend) and using the Advantage Klentaq Polymerase Mix (Clontech) which contains a TaqStart Antibody to provide automatic hot start PCR (Kellogg et al., *Biotechniques* 16:1134–1137 (1994), which is hereby incorporated by reference). PCR was optimized using the control reagents contained in the PCR-Select cDNA subtraction kit as template and the OPTI-PRIME™ PCR Optimization Kit (Stratagene). Amplification products were analyzed by gel electrophoresis (Sambrook et al., *Molecular Cloning: A Laboratory Manual*, 2nd ed., Cold Spring Harbor, N.Y.:Cold Spring Harbor Laboratory Press (1987) ("Sambrook") and Ausubel et al., *Current Protocols in Molecular Biology*, New York:Greene Publishing Associates and Wiley-Interscience (1990) ("Ausubel"), which are hereby incorporated by reference). In our hands, the optimal buffer for primary PCR contained 40 mM Tricine-KOH (pH 9.2), 15 mM KOAc, 3.5 mM Mg(OAc)$_2$, and 75 mg/ml bovine serum albumin (10×Klentaq PCR reaction buffer, Clontech). The optimal buffer for secondary PCR contained 10 mM Tris-HCl (pH 8.3), 75 mM KCl, and 3.5 mM MgCl$_2$ (Stratagene, Opti-Prime 1×Buffer #4) with 5% dimethylsulfoxide.

Example 2

Cloning of the Subtracted cDNAs

Nested PCR primer 1 was phosphorylated using reagents from Invitrogen (Eukaryotic TA Cloning Kit, Unidirectional). Secondary PCR (10 cycles) was performed in the optimized buffer described above using nested PCR primer 2 and the phosphorylated nested PCR primer 1. PCR products were directionally ligated into the mammalian expression TA cloning vector pCR ™ 3.1-Uni and transformed into TOP10F' competent cells using general techniques (Sambrook and Ausubel, which are hereby incorporated by reference) and commercial reagents from InVitrogen. PCR™ 3.1-Uni contains a T-overhang which allows the direct cloning of PCR products containing single 3' A-overhangs (Mead et al., *Bio/Technology* 9:657–663 (1991), which is hereby incorporated by reference. Transformed cells were selected in Luria-Broth media containing 25 mg/ml kanamycin.

Example 3

Sequencing of Differentially Expressed Clones

DNA plasmid isolations were performed using the Qiagen Plasmid Mini Kit which employs the alkaline lysis method (Sambrook, which is hereby incorporated by reference). Plasmids were screened for insert sequences using nested PCR primers 1 and 2 and the protocol and reagents from the Geneamp PCR Kit (Perkin Elmer), and amplified products were analyzed by gel electrophoresis. Clones containing inserts greater than 100 basepairs ("bp") were obtained for sequencing analysis. Dideoxy DNA sequencing was performed using the Applied Biosystems Model 373 Automated DNA Sequencing System. The DNA sequence of each strand was determined using sequencing primers T7 (5' TAATAC-GACTCACTATAGGG 3') (SEQ ID NO:12) and pCR™ 3.1 Reverse (5' TAGAAGGCACAGTCGAGG 3') (SEQ ID NO:13), respectively.

Example 4

Search for Genetic Homologies

GenBank was searched for homologous sequences via the program BLASTN (Altschul et al., *J. Mol. Biol.* 215:403–410 (1990) and Benson et al., *Nucleic Acids Res.* 24:1–5 (1996), which are hereby incorporated by reference). Sequences were classified as known or unknown based on the resulting score and probability values. Known sequences were arbitrarily defined as those having probability values greater than 0.05 (p>0.05) relative to database sequences or those showing homology to non-human species or to cosmids containing human DNA of which a function has not been assigned.

Example 5

Rapid Amplification of cDNA Ends

Full length mammary associated chemokine ("MACK") cDNA was generated using 5' and 3' rapid amplification of cDNA ends ("RACE") (Frohman, *PCR Protocols*, New York:Academic Press, pp. 28–39 (1990), which is hereby incorporated by reference) using commercial reagents (Marathon cDNA Amplification Kit, Clontech). Human mammary gland polyA RNA (Clontech) was used as a template for first and second strand cDNA synthesis, and adaptors were ligated to the pool of cDNA according to the manufacturer's protocol. The 3' RACE product was obtained by using the gene-specific primer (24R) 5' ACTGGGAT-TATAGGTGTGAGCC 3' (SEQ ID NO:14) and Clontech's adaptor primer 1 (AP1) using "Touchdown PCR" according to the manufacturer's directions. This was followed by a secondary PCR using the nested gene-specific primer (24R2) 5' CAAATTCAGGTTTAATGTTTTTGG 3' (SEQ ID NO:15) and Clontech's nested adaptor primer 2 (AP2). PCR products were cloned into the T/A cloning vector pCR2.1 (Invitrogen). DNA plasmid preparations were prepared and sequenced using vector sequences T7 and M13 reverse. Internal sequencing primers were based on confirmed sequences.

The 5' RACE product was obtained using Clontech's MARATHON™ Ready cDNA from human mammary gland according to their protocol. "Touchdown PCR" was performed on the cDNA using gene-specific primer (F4) 5' CTCAAACGTGTGAGCCCGGCA 3' (SEQ ID NO:16) and AP1, and nested PCR was performed using nested gene-specific primer (F3) 5' GCTACTCAAACTA-GACGTTTTGAAG 3' (SEQ ID NO:17) or (F1) 5' GAAT-TCACGTAGGAAATTCTTAACC 3' (SEQ ID NO:9) and AP2 (see above). PCR products were cloned and sequenced as described above. A consensus sequence was generated using programs from the Hitachi software package DNAsis for Windows.

Example 6

Northern Blot Analysis

Human mammary gland PolyA+RNA (3 μg, Clontech Laboratories, Inc.) was separated and transferred using the NORTHERNMAX™ Northern Blotting Kit from Ambion.

PCR amplification of a 302 bp region within the predicted ORF was performed using primers F85' CCGTAT-GTTTCGTGTTTCCCCTGA 3' (SEQ ID NO:18) and R5 5' AGCCATACTTCCCATTGCCTCCAG 3' (SEQ ID NO:19) and 5' RACE clone (#27) as template. This fragment was directionally ligated to a T7 promoter (LIG'NSCRIBE™ RNA Polymerase Promoter Addition Kit, Ambion) and amplified such that the antisense strand was orientated immediately downstream to the T7 promoter according to the manufacturer's protocol. An antisense riboprobe having SEQ ID NO:11 was transcribed in vitro using T7 RNA polymerase, and labeled using the BRIGHTSTAR™ Psoralen-Biotin Nonisotopic Labeling Kit (Ambion). Hybridization and chemiluminescent detection were performed using protocols from Ambion's NORTHERN-MAX™ and BRIGHTSTAR™ BIODETECT™ Kits, respectively.

Example 7

Production of Antisera to the Open Reading Frame Protein Sequence

The predicted open reading frame within the MACK gene was determined using commercial software (DNAsis, Hitahci Corp.). Synthetic peptides corresponding to predicted immunogenic domains, KLH-peptide conjugates and resultant rabbit antisera were produced by Research Genetics, Inc. (Huntsville, Ala.). Antisera were collected after a 10-week immunization protocol.

Example 8

Titration of Anti-peptide Antisera

Synthetic peptides were dissolved in 0.2 M carbonate-bicarbonate buffer, pH 9.4 (CBC buffer) at a concentration of 10 µg/mL. Microplates were coated (100 (µL/well) with the peptides at 4° C. for 18 hrs. The solution was removed and the microwells were blocked with 1% bovine serum albumin in tris-buffered saline ("TBS"), pH 7.4 for 1 hr. Dilutions of anti-peptide antisera were incubated with the solid-phase peptides for 1 hr, and, following a wash procedure, goat antibodies to rabbit immunoglobulin (biotin-conjugated) were added for 30 min. After another wash procedure, each well received 100 µL of avidin-biotinylated alkaline phosphatase complex (ABC Kit, Pierce Immunochemicals) for 30 min. Thereafter, the wells were washed, and substrate (para-nitrophenyl phosphate, 1 mg/ml in diethanolamine buffer, pH 9.8) was added for 30 min. After stopping the reactions with 50 µL of 5 N NaOH, optical density was determined at an absorbance of 450 nm using a microplate spectophotometer.

Example 9

Purification of IgG and Enzyme Coupling

IgG from rabbit serum was purified using protein A affinity chromatography (MAPS II Kit, Bio-Rad Labs). IgG was conjugated to horseradish peroxidase using the periodate oxidation technique (Nakane et al., *J. Histochem. Cytochem.* 22:1084–1091 (1974), which is hereby incorporated by reference).

Example 10

SDS-PAGE and Western Blotting

SDS-PAGE was performed as described in Laemmli, *Nature* 227:680–685 (1970) ("Laemmli"), which is hereby incorporated by reference.

Western blotting was performed essentially as described in Papsidero et al., *Hybridoma* 7:117–128 (1988), which is hereby incorporated by reference, using nitrocellulose paper with a 0.22 µm pore size. Blots were incubated for 1 hr at room temperature with immune or pre-immune sera diluted in assay buffer. The membranes were washed and developed with avidin-biotin-alkaline phosphatase reagents using commercial reagents (ABC Kit, Pierce Immunochemicals). Blots were developed with insoluble substrate (BCIP/NBT solution, Pierce Immunochemicals), washed in water and air-dried.

Example 11

Results of Comparison of Isolated Sequence Tags to GenBank

Human breast tissue mRNA was subjected to SSH and 118 sequence tags were isolated and sequenced. Of the total examined, 62% (73 of 118) were homologous to genes found in the GenBank database (Table 3). Of interest, approximately 14% (10 of 73) of the previously described sequences were breast tissue specific or highly associated with breast tissue (i.e., casein isoforms, alpha-lactalbumin, and milk fat globule proteins). Remarkably, 38% of the sequence tags (45 of 118) demonstrated no significant homology with genes found in the database (Table 3). These novel genes were studied further using RT-PCR in order to determine the specificity of their tissue expression.

TABLE 3

Human Breast Tissue mRNA Sequence Tags Isolated Using Suppression Subtraction Hybridization

| ID # | GenBank Search | insert size (bp) | Strongest Homology | Blast Score (probability) | Identical residues/Total residues (%) |
|---|---|---|---|---|---|
| 1 | Known | 309 | Human keratin | 459 (p < 0.001) | 99/108 (91%) |
| 5 | Known | 195 | Human A1S9 mRNA | 619 (p < 0.001) | 127/133 (95%) |
| 7 | Known | 66 | Human Vimentin | 330 (p < 0.001) | 66/66 (100%) |
| 8 | Unknown | 198 | *S. cerevisiae* | 114 (p = 1.0) | 30/39 (76%) |
| 10 | Known | 96 | *H. sapiens* rho GAP protein | 462 (p < 0.001) | 95/98 (96%) |
| 11 | Known | 105 | Mouse cerbA alpha 2 mRNA (thyroid H.) | 507 (p < 0.001) | 105/105 (100%) |
| 14 | Known | 135 | TCR eta = Tcell receptor eta chain | 258 (p < 0.001) | 62/75 (82%) |
| 16 | Known | 115 | Pancreatic peptidylglycine | 557 (p < 0.001) | 113/115 (98%) |
| 20 | Known | 182 | *H. sapiens* paraoxynase | 520 (p < 0.001) | 122/146 (83%) |

TABLE 3-continued

Human Breast Tissue mRNA Sequence Tags Isolated Using Suppression Subtraction Hybridization

| ID # | GenBank Search | insert size (bp) | Strongest Homology | Blast Score (probability) | Identical residues/Total residues (%) |
|---|---|---|---|---|---|
| 22 | Known | 194 | Human mRNA for cytoskeletal gamma actin | 956 (p < 0.001) | 192/194 (99%) |
| 23 | Unknown | 201 | Chimpanzee cmyc protooncogene | 134 (p = 0.18) | 42/61 (68%) |
| 28 | Known | 150 | Milk fat globule protein (human) | 515 (p < 0.001) | 103/103 (100%) |
| 30 | Known | 442 | H. sapiens mitochondrial genome | 1245 (p < 0.001) | 251/254 (98%) |
| 47 & 67 | Unknown | 143 | Beet necrotic yellow vein virus | 134 (p = 0.10) | 54/88 (61%) |
| 51 | Known | 174 | H. sapiens mRNA homologue to yeast ribo. Protein | 831 (p < 0.001) | 169/174 (97%) |
| 54 | Unknown | 125 | M. musculus for Notch 3 | 179 (p < 0.001) | 45/57 (78%) |
| 57 | Known | 180 | H. sapiens cDNA for betacasein | 715 (p < 0.001) | 147/155 (94%) |
| 60 | Unknown | 202 | X. laevis mRNA for DNA binding | 122 (p = 0.88) | 42/64 (65%) |
| 61 | Known | 286 | Human 28k basic protein | 1349 (p < 0.001) | 273/278 (98%) |
| 62 | Known | 195 | Human A1S9 mRNA | 968 (p < 0.001) | 194/195 (99%) |
| 74 | Known | 152 | Human MER 37 transposable element | 351 (p < 0.001) | 87/108 (80%) |
| 75 | Known | 192 | Human mRNA for cytoskeletal gamma actin | 960 (p < 0.001) | 192/192 (100%) |
| 78 | Unknown | 626 | C. elegans ZK1073 | 123 (p = 1.0) | 31/39 (79%) |
| 79 & 80 | Unknown | 90 & 100 | Myxococcus xanthus photolyase | 113 (p = 0.96) | 29/37 (78%) |
| 82 | Unknown | 295 | Actinobacillus riboflavin biosynthesis operon | 121 (p = 0.99) | 41/62 (66%) |
| 89 | Known | 214 | Human casK mRNA for Kappa casein | 1063 (p < 0.001) | 213/214 (99%) |
| 101 | Unknown | 99 | C. elegans C35B8 | 118 (p = 0.71) | 34/47 (72%) |
| 105 | Known | 84 | H. sapiens mRNA for 90K product | 357 (p < 0.001) | 75/84 (89%) |
| 114 | Unknown | 111 | Human peregrin mRNA | 127 (p = 0.23) | 39/56 (69%) |
| 115 | Known | 186 | Rat 8s RNA | 728 (p < 0.001) | 147/151 (97%) |
| 116 | Unknown | 413 | M. musculus for p38264 | 787 (p < 0.001) | 171/190 (99%) |
| 120 | Known | 253 | Human SF 2 p33 mRNA (splicing factor) | 1223 (p < 0.001) | 247/253 (97%) |
| 121 | Unknown | 154 | M. musculus serum inducible | 653 (p < 0.001) | 141/154 (91%) |
| 122 | Unknown | 354 | Drosophila silver p. | 264 (p < 0.001) | 118/202 (58%) |
| 127 | Known | 133 | H. sapiens mRNA for rat HREV 107like | 368 (p < 0.001) | 96/125 (76%) |
| 131 | Unknown | 117 | C. elegans R12C12 | 126 (p = 0.31) | 38/54 (70%) |
| 133 | Unknown | 133 | Bos taurus polymeric immunoglobulin | 149 (p < 0.001) | 33/37 (89%) |
| 135 | Unknown | 124 | Rat vesicle associated membrane protein | 286 (p < 0.001) | 60/64 (93%) |
| 140 | Known | 312 | Human ferritin | 1530 (p < 0.001) | 308/312 (98%) |
| 142 | Unknown | 123 | Human MAGE 4a antigen gene | 129 (p = 0.21) | 37/51 (72%) |
| 143 | Known | 94 | Human ribosomal protein L28 | 470 (p < 0.001) | 94/94 (100%) |
| 145 | Unknown | 283 | M. auratus beta myosin | 132 (p = 0.39) | 52/84 (61%) |
| 152 | Known | 551 | H. sapiens mitochondrial genome | 751 (p < 0.001) | 153/157 (97%) |
| 155 | Unknown | 238 | R. norvecigus adenylyl cyclase | 109 (p = 0.87) | 35/52 (67%) |
| 158 | Known | 186 | Rat 8s RNA | 698 (p < 0.001) | 142/146 (97%) |
| 162 | Known | 129 | Gamma actin | 629 (p < 0.001) | 127/129 (98%) |
| 164 | Known | 95 | Human mRNA for OSF1 | 452 (p < 0.001) | 92/95 (96%) |
| 171 | Known | 321 | Human mRNA for cytokeratin | 1033 (p < 0.001) | 209/213 (98%) |
| 175 | Unknown | 134 | M. musculus isocitrate dehydrogenase | 130 (p = 0.19) | 36/49 (73%) |
| 176 | Known | 150 | Human mitochondrial DNA | 750 (p < 0.001) | 150/150 (100%) |
| 178 | Unknown | 269 | Gorilla ALU repeat/H. sapiens casein kinase | 191 (p < 0.001) | 47/60 (78%) |
| 179 | Known | 182 | Human COREI protein | 903 (p < 0.001) | 181/182 (99%) |
| 181 | Known | 155 | Human alphalactalbumin | 712 (p < 0.001) | 144/147 (97%) |
| 182 & 197 | Unknown | 259 | Human DNA sequence from cosmid N28H9 | 196 (p < 0.001) | 78/127 (61%) |
| 188 | Known | 216 | Human ALU | 453 (p < 0.001) | 101/114 (88%) |
| 189 | Unknown | 105 | Human DNA sequence from cosmid N37F | 125 (p < 0.001) | 31/39 (79%) |
| 192 | Unknown | 104 | M. musculus cytoplasmic protein | 119 (p = 0.62) | 27/31 (87%) |
| 195 | Known | 155 | Human alphalactalbumin | 696 (p < 0.001) | 144/147 (97%) |
| 196 | Known | 156 | Mouse 28s rRNA | 412 (p < 0.001) | 84/86 (97%) |
| 201 | Known | 183 | Human COREI protein | 841 (p < 0.001) | 169/171 (98%) |
| 204 | Unknown | 194 | Human DNA sequence from cosmid L139H | 514 (p < 0.001) | 118/138 (85%) |
| 205 | Known | 54 | Human cytokeratin | 238 (p < 0.001) | 48/49 (97%) |
| 207 | Known | 139 | Human prostasin | 589 (p < 0.001) | 119/121 (98%) |
| 208 | Unknown | 356 | Human cathepsin D (catD) gene | 130 (p = 0.64) | 34/44 (75%) |
| 209 | Known | 373 | Putative zinc finger Rattus norxecigus | 707 (p < 0.001) | 161/195 (82%) |
| 210 | Known | 129 | Gamma actin | 606 (p < 0.001) | 124/129 (97%) |
| 214 | Known | 105 | Alphalactalbumin | 509 (p < 0.001) | 103/105 (98%) |
| 216 | Known | 153 | Alphalactalbumin | 709 (p < 0.001) | 143/145 (98%) |

TABLE 3-continued

Human Breast Tissue mRNA Sequence Tags Isolated
Using Suppression Subtraction Hybridization

| ID # | GenBank Search | insert size (bp) | Strongest Homology | Blast Score (probability) | Identical residues/Total residues (%) |
|---|---|---|---|---|---|
| 218 | Known | 190 | Acidic calponin | 941 (p < 0.001) | 189/190 (99%) |
| 220 | Unknown | 99 | C. elegans cosmid C34E7 | 108 (p = 1.0) | 28/36 (77%) |
| 221 | Unknown | 122 | S. cerevisiae chromosome | 121 (p = 0.33) | 22/25 (87%) |
| 223 | Unknown | 91 | Bovine betahydroxylase | 113 (p = 0.94) | 29/37 (78%) |
| 224 | Known | 164 | Lactate dehydrogenase | 614 (p < 0.001) | 124/127 (97%) |
| 225 | Known | 273 | Proalpha collagen | 1335 (p < 0.001) | 269/273 (98%) |
| 229 | Known | 235 | Collagen | 1143 (p < 0.001) | 232/235 (98%) |
| 230 | Unknown | 117 | Plasmodium falciparum (strain FCR3) | 116 (p = 0.89) | 30/39 (76%) |
| 231 & 234 | Unknown | 94 | CNS myelin P0like glycoprotein | 124 (p = 0.26) | 40/59 (67%) |
| 232 | Unknown | 405 | H. sapiens mRNA for 218kD Mi2 protein | 132 (p = 0.55) | 42/62 (67%) |
| 233 | Unknown | 198 | Rat TnT gene encoding troponin T | 130 (p = 0.36) | 34/44 (77%) |
| 238 | Known | 140 | Human Thy 1 glycoprotein | 645 (p < 0.001) | 133/140 (95%) |
| 242 | Known | 136 | H. sapiens casK mRNA for Kappa casein | 666 (p < 0.001) | 134/136 (98%) |
| 249 | Known | 136 | H. sapiens casK mRNA for Kappa casein | 680 (p < 0.001) | 136/136 (100%) |
| 250 | Known | 288 | H. sapiens CpG DNA | 792 (p < 0.001) | 164/172 (95%) |
| 252 | Known | 525 | Human pHL1 gene (cmyc oncogene) | 1704 (p < 0.001) | 352/377 (93%) |
| 253 | Known | 125 | Human mRNA for plasma gelsolin | 618 (p < 0.001) | 124/125 (99%) |
| 255 | Known | 138 | Human Xq 28 genomic DNA | 333 (p < 0.001) | 69/74 (93%) |
| 256 | Known | 56 | Human vimentin | 280 (p < 0.001) | 55/55 (100%) |
| 257 | Known | 236 | Human breast cancer LIV1 regulated mRNA | 1134 (p < 0.001) | 230/236 (97%) |
| 258 | Known | 125 | Human gelsolin | 618 (p < 0.001) | 124/125 (99%) |
| 261 | Known | 283 | Human mRNA for ORF myeloblast celline | 1394 (p < 0.001) | 280/283 (98%) |
| 263 | Known | 156 | Human phemphigoid autoantigen | 773 (p < 0.001) | 155/156 (99%) |
| 264 | Unknown | 198 | C. elegans N2 basichelix | 116 (p = 0.99) | 36/52 (69%) |
| 269 | Unknown | | No Matches Identified | N/A | N/A |
| 275 | Known | 283 | Human mRNA for ORF | 1373 (p < 0.001) | 277/283 (97%) |
| 276 | Unknown | 195 | C. elegans cosmid ZK813 | 133 (p = 0.20) | 41/59 (69%) |
| 279 | Known | 339 | Alpha casein | 1674 (p < 0.001) | 336/339 (99%) |
| 284 | Known | 129 | H. sapiens BTF2p44 mRNA for basic transcription | 645 (p < 0.001) | 129/129 (100%) |
| 287 | Known | 293 | Human mRNA | 1251 (p < 0.001) | 261/280 (93%) |
| 291 | Unknown | 171 | D. melanogaster chromosome 3 locus 85D | 133 (p = 0.18) | 33/41 (80%) |
| 292 | Known | 148 | H. sapiens HIV1 TAR RNA binding protein | 699 (p < 0.001) | 143/148 (96%) |
| 297 | Known | 136 | Human migration inhibitory factor mRNA | 617 (p < 0.001) | 127/136 (93%) |
| 300 | Unknown | 176 | R. norvegicus FSHregulated protein mRNA | 427 (p < 0.001) | 91/98 (92%) |
| 302 | Unknown | 96 | S. platensis rpsB gene (ribosomal protein S2) | 111 (p = 0.99) | 43/69 (62%) |
| 303 | Known | 146 | H. sapiens alphalactalbumin | 705 (p < 0.001) | 141/141 (100%) |
| 305 | Known | 99 | B. taurus myosin IB mRNA | 336 (p < 0.001) | 80/99 (80%) |
| 308 | Unknown | 295 | D. melanogaster Oregon R mRNA | 422 (p < 0.001) | 134/197 (68%) |
| 314 | Unknown | 158 | Maize mRNA for catalase 2 | 113 (p = 1.0) | 29/37 (78%) |
| 329 | Unknown | 160 | C. elegans cosmid C09B9 | 117 (p = 0.97) | 39/59 (66%) |
| 330 | Known | 109 | Human nonmuscle myosin alkali light chain | 531 (p < 0.001) | 107/109 (98%) |
| 333 | Unknown | 119 | Mouse MA3 (apoptosisrelated gene) mRNA | 124 (p = 0.39) | 30/37 (81%) |
| 337 | Unknown | 99 | No Matches Identified | N/A | N/A |
| 338 | Unknown | 271 | Human fur gene, exons 1 through 8 | 143 (p = 0.057) | 51/79 (64%) |
| 339 | Known | 65 | H. sapiens mRNA for IgG1 heavy chain | 123 (p = 0.012) | 35/48 (72%) |

At least one expressed sequence tag (Table 3, ID #189), designated Breast Sequence Tag-24 (BRST-24"), was demonstrated to exhibit a high level of specificity to breast tissue. BRST-24 has SEQ ID NO:35 as follows:

ACACGAATTCACGTAGGAAATTCTTAACCAAAAACATTAAACCTGAATTTG

ATCACAAGAAAATAATTAGGCCAGGCACTGTGGCTCACACCTATAATCCCA

GT

Example 12

Tissue Specificity Analysis of BRST-24 Using RT-PCR

The tissue specificity of BRST-24 was experimentally demonstrated using RT-PCR analysis of various human tissue mRNAs along with primers which are complementary to regions of the BRST-24 nucleotide sequence. The primers had the following sequences:

```
GAATTCACGTAGGAAATTCTTAACC (F1 primer)

ACTGGGATTATAGGTGTGAGCC (R1 primer)
```

These sequences are respectively identified herein as SEQ ID NO:9 and SEQ ID NO:10.

Example 13

Detection of BRST-24 Using RT-PCR Analysis of Human Tissues

RT-PCR was performed using the protocol and reagents from the Perkin-Elmer GeneAmp EZ rTth RNA PCR Kit. PCR primers BRST-24 fwd (5' GAATTCACGTAGGAAAT TCTTAACC 3') (SEQ ID NO:9) and BRST-24 rev (5' ACTGGGATTATAGGTGTGAGCC 3') (SEQ ID NO:10) were synthesized by Research Genetics. A tissue panel of total RNAs derived from human testis, brain, lung, prostate, kidney, skeletal muscle, small intestine, liver, pancreas, uterus, and breast (all obtained from Clontech) was screened via RT-PCR for the presence of BRST-24 using a Perkin-Elmer DNA Thermal Cycler Model 2400. Reverse transcription was carried out for 30 minutes at 60° C., the reaction mix was denatured at 94° C. for one minute followed by 40 cycles of PCR (94° C., 15 seconds (denature), 60° C., 30 seconds (anneal and extend)), and a final extension was carried out for 7.0 minutes at 60° C. The amplified products were observed on a 3% agarose gel (0.5×TBE) as described in Sambrook, which is hereby incorporated by reference.

As shown in Table 4, the BRST-24 primer pair was able to be utilized to amplify nucleotide sequences from all of three specimens of human breast tissue mRNA using RT-PCR. These specimens included two normal breast tissue pools and one specimen of invasive ductal carcinoma. Other human tissue mRNAs examined were noted to contain no detectable, amplifiable mRNA genetic sequences corresponding to BRST-24. These tissues included liver, lung, small intestine, pancreas, uterus, brain, kidney, and skeletal muscle. A testes specimen did, however, produce a faint reaction product. As an experimental control, mRNA sequences specific for prostate specific antigen ("PSA") were detected by RT-PCR using primers homologous to regions within the PSA nucleic acid sequence (Deguchi et al., Cancer Research 53:5350–5354 (1993), which is hereby incorporated by reference). As seen in Table 4, PSA mRNA was exclusively detected in human prostate tissue, confirming the specificity of the PSA mRNA expression and the integrity of the experimental protocol.

TABLE 4

Differential Expression of BRST-24 and PSA Transcripts in Human Tissues as Detected Using RT-PCR

| Tissue | Normal/ Malignant | BRST-24[4] Expression | PSA[5] Expression |
| --- | --- | --- | --- |
| Breast[1] | Normal | 2+[6] | ND[7] |
| Breast[2] | Normal | 2+ | — |
| Breast[3] | Carcinoma | 2+ | ND |
| Prostate | Normal | — | 2+ |
| Kidney | Normal | — | — |
| Pancreas | Normal | — | — |
| Small Intestine | Normal | — | — |
| Skeletal Muscle | Normal | — | — |
| Testis | Normal | +/− | — |
| Brain | Normal | — | — |
| Uterus | Normal | — | — |
| Liver | Normal | — | — |
| Pancreas | Normal | — | — |

[1]Human mammary gland poly A+ RNA isolated from a pool of 4 specimens (Caucasian, ages 34–49).
[2]Human mammary gland total RNA isolated from a pool of 6 specimens (Caucasian, ages 16–35).
[3]Total RNA isolated from an invasive ductal carcinoma of the breast (Asian, age 36).
[4]RT-PCR using primer pair specific for BRST-24 (SEQ ID Nos: 9 and 10)
[5]RT-PCR using primer pairs specific for Prostate Specific Antigen (Deguchi et al., CancerResearch 53:5350-5354 (1993), which is hereby incorporated by reference).
[6]−, negative; +/−, equivocal; 1+, weak; 2+, strong reaction product.
[7]ND, not done.

Expression of BR-24 transcript was also monitored using Northern blotting with an internal probe from the BR-24 cDNA sequence having a sequence corresponding to S SEQ ID NO:11.

Northern blot analysis of polyA RNA from human mammary gland resulted in the detection of a transcript appearing slightly above the 3000 base pair marker. This is consistent with the predicted transcript size based upon results from RACE construction of the full-length cDNA.

BR-24 nucleic acid sequences were also detected in human cell lines using RT-PCR along with the same primers used in the above experiments. Results as, seen in Table 5, provide additional support to the view that the BR-24 gene is expressed preferentially in human mammary cells.

TABLE 5

Detection of BR-24 Transcripts in Cultured Human Cell Lines

| Cell Line | Description | Expression of BR-24 Transcripts |
| --- | --- | --- |
| BT-20 | Breast Carcinoma | 2+ |
| MCF-7 | Breast Carcinoma | 1+ |
| MDA-MB-157 | Breast Carcinoma | — |
| SK-OV-3 | Ovary Carcinoma | — |
| LNCaP | Prostate Carcinoma | — |
| SW620 | Colon Carcinoma | 1+− |

Example 14

Isolation of the Full-length BR-24 cDNA

To obtain the full-length cDNA sequence of MACK, the 5' and 3' RACE clones were overlapped. Thus, this sequence represents the consensus of 5' and 3' RACE clones from a population of donor mRNAs. The 5' RACE clones varied in length at the 5' end which may be attributed to secondary structure and pausing of the reverse transcription during cDNA synthesis. Using this method, a consensus cDNA sequence of 3117 base pairs, excluding the polyA tail was generated. This sequence is identified herein as SEQ ID NO:6.

Using computer algorithms (DNASis software package, Hitachi Corp.), the open reading frame was determined to encode a protein of 127 amino acids, between nucleic acid bases 47 and 428 above. The amino acid sequence of this protein is identified herein as SEQ ID NO:1. The deduced molecular weight of the protein was 14,232 daltons, and the deduced isoionic point was pH 10.44.

Of interest, the above protein sequence shared sequence homology with a class of cytokines designated as "chemokines" (See Baggiolini et al., *Ann. Rev. Immunol.* 15:675–705 (1997) and Rollins, *Blood* 90:909–928 (1997), which are hereby incorporated by reference. Thus, the above sequence represents a new member of the "CC" or "BB" class of chemokines. FIG. 1 shows alignment of the MACK amino acid sequence with other members of the CC chemokine family. Of significance, the identification of cytokines in human milk is of great interest and is a topic which has been recently investigated (Srivastava et al., *Res. Commun. Molec. Path. Pharm.* 93:263–283 (1996), which is hereby incorporated by reference).

Example 15

Specificity of Anti-peptide Antisera

Rabbit antisera were raised against three regions (underlined type) of the MACK protein sequence (SEQ ID NO:1):

MQQRGLAIVA LAVCAALHAS EAILPIASSC CTEVSHHISR

RLLERVNMCR IQRADGDCDL AAVILHVKRX RICVSPHNHT

VKQWMKVQAA XKNGKGNVCH RKKHHGKRNS

NRAHQGKHET YGHKTPY

The sequence corresponding to amino acids 32–49 of the MACK protein was designated "MACK A" and has an amino acid sequence corresponding to SEQ ID NO:3. The sequence corresponding to amino acids 92–107 of the MACK protein was designated "MACK B" and has an amino acid sequence corresponding to SEQ ID NO:4. The sequence corresponding to amino acids 109–127 of the MACK protein was designated "MACK C" and has an amino acid sequence corresponding to SEQ ID NO:5.

Antisera against their respective peptides demonstrated high titer, up to dilutions of over 100,000. In addition, anti-peptide antisera reacted with a high degree of specificity to their corresponding immunogen.

To determine if antisera raised against peptides from the deduced protein sequence of the MACK protein recognized the native protein, Western blotting experiments were performed. Inasmuch as the prostate tissue specific protein PSA is found in the secretion of the prostate gland (i.e., seminal fluid), it was suspected that the MACK protein would be detectable in the secretion of the mammary gland. Of interest, when samples of human milk were examined on Western blotting versus the anti-MACK peptide antisera, each of 6 specimens was noted to contain an immunoreactive protein of having an experimentally determined weight of approximately 16–17 kDa. This band was not present when control blots were allowed to react with non-immune rabbit sera, suggesting specificity associated with the use of the anti-MACK peptide antisera. This specificity was confirmed using absorption experiments with soluble peptides. Following absorption of the anti-sera with soluble peptides (100 μg per ml of antiserum dilution), the specific immunoreactive band was abrogated (not shown).

Example 16

Detection of Mammary Associated Chemokine (MACK) in Breast Cancer

Sera Using Western Blotting

Aliquots (1.5 μl) of human sera were heated to 100° C. for 15 min in the presence of reducing agent (mercaptoethanol) and denaturant (sodium dodecyl sulfate ("SDS")) and were then subjected to SDS-polyacrylamide gel electrophoresis ("SDS-PAGE") (as described in Laemmli, which is hereby incorporated by reference) in a 15% PAGE gel. After electrophoresis, the separated proteins were transferred to a nitrocellulose membrane (0.2 μm pore) (Towbin et al., *Proc. Natl. Acad. Sci. U.S.A.*, 76:4350–4354 (1979), which is hereby incorporated by reference). Non-specific protein binding sites on the membrane were blocked with a solution containing bovine serum albumin ("BSA") (2% in tris-buffered saline, pH 7.4) for 1 hr. Thereafter, the membrane was allowed to react for 1 hr with a 1/1000 dilution of polyclonal (rabbit) antisera raised against synthetic peptides corresponding to regions of the MACK gene product, as described in Examples 7 and 15. The membrane was washed thrice in tris-buffered saline and developed with avidin-biotin complex reagents (Pierce Chemicals) according to the recommendations of the manufacturer. Specific bands were revealed following the addition of insoluble alkaline phosphatase substrate (BCIP/NBT).

The results, presented in Table 6, demonstrated the occurrence of two protein bands (one at 20–30 kDa and one at 7–12 kDa) specifically found in sera obtained from patients with breast cancer. Of 31 such specimens examined, 30 sera demonstrated both bands, while one specimen (number 1871) demonstrated the 20–30 kDa band only. In comparison, none of 10 serum specimens obtained from patients with lymphoma or with prostatic, ovarian, lung, or colon cancers showed either of the specific bands when allowed to react with the antibodies to MACK. In addition, MACK peptide bands were not seen in sera obtained from 7 normal individuals (Table 6). These results demonstrate that MACK or MACK-associated proteins are found in the circulation of individuals with cancer of the breast and that detection of these immunoreactivities can be of diagnostic and/or monitoring value for the disease.

TABLE 6

| Sample ID | Diagnosis | Stage | High Band[1] | Low Band[2] |
|---|---|---|---|---|
| 1008 | Breast Cancer | unknown | + | + |
| 1869 | Breast Cancer | 3 | + | + |
| 1870 | Breast Cancer | 3 | + | + |
| 1871 | Breast Cancer | 3 | + | − |
| 1872 | Breast Cancer | 3 | + | + |
| 1873 | Breast Cancer | 3 | + | + |
| 1874 | Breast Cancer | 3 | + | + |
| 1875 | Breast Cancer | 3 | + | + |
| 1876 | Breast Cancer | 3 | + | + |

TABLE 6-continued

| Sample ID | Diagnosis | Stage | High Band[1] | Low Band[2] |
|---|---|---|---|---|
| 1877 | Breast Cancer | 3 | + | + |
| 1878 | Breast Cancer | 3 | + | + |
| 1293 | Breast Cancer | unknown | + | + |
| 1294 | Breast Cancer | unknown | + | + |
| 1296 | Breast Cancer | unknown | + | + |
| 1297 | Breast Cancer | unknown | + | + |
| 1298 | Breast Cancer | unknown | + | + |
| 1299 | Breast Cancer | unknown | + | + |
| 1300 | Breast Cancer | unknown | + | + |
| 1301 | Breast Cancer | unknown | + | + |
| 1302 | Breast Cancer | unknown | + | + |
| 1303 | Breast Cancer | unknown | + | + |
| 2694 | Breast Cancer | 2 | + | + |
| 2697 | Breast Cancer | 2 | + | + |
| 2698 | Breast Cancer | 2 | + | + |
| 4681 | Breast Cancer | 2 | + | + |
| 4682 | Breast Cancer | 2 | + | + |
| 4683 | Breast Cancer | 2 | + | + |
| 4684 | Breast Cancer | 2 | + | + |
| 4686 | Breast Cancer | 2 | + | + |
| 4687 | Breast Cancer | 2 | + | + |
| 4688 | Breast Cancer | 2 | + | + |
| 258 | Lung Cancer | 3 | − | − |
| 259 | Lung Cancer | 2 | − | − |
| 469 | Lymphoma | unknown | − | − |
| 470 | Lymphoma | unknown | − | − |
| 2486 | Prostate Cancer | D | − | − |
| 2488 | Prostate Cancer | D | − | − |
| 1939 | Ovarian Cancer | 4 | − | − |
| 1940 | Ovarian Cancer | 4 | − | − |
| 1554 | Colon Cancer | C2 | − | − |
| 1574 | Colon Cancer | C2 | − | − |
| 1001 | Normal | | − | − |
| 1002 | Normal | | − | − |
| 1003 | Normal | | − | − |
| 1004 | Normal | | − | − |
| 1005 | Normal | | − | − |
| 1006 | Normal | | − | − |
| 1007 | Normal | | − | − |

[1]High MW Band, approx. 20–30 kDa
[2]Low MW Band, approx. 7–12 kDa

Although the invention has been described in detail for the purpose of illustration, it is understood that such detail is solely for that purpose and variations can be made by those skilled in the art without departing from the spirit and scope of the invention which is defined by the following claims.

What is claimed:

1. A method for diagnosing breast cancer in a patient, which method comprises detecting expression of a chemokine polypeptide in a sample of tissue or body fluid of the patient, wherein the chemokine polypeptide has the amino acid sequence as depicted in SEQ ID NO:2, which method comprises detecting binding of an antibody or antigen binding portion thereof to said chemokine polypeptide.

2. The method according to claim 1, wherein the antibody or binding portion thereof is detectably labeled.

3. The method according to claim 1, wherein the detection is in vitro.

4. The method according to claim 1, wherein the detection is in vivo.

5. The method according to claim 1, wherein the tissue or body fluid is a blood specimen.

6. The method according to claim 1, wherein the tissue or body fluid is a biopsy specimen.

7. The method according to claim 1, wherein the tissue or body fluid is from the breast.

* * * * *

SEQUENCE LISTING

<160> NUMBER OF SEQ ID NOS: 35

<210> SEQ ID NO 1
<211> LENGTH: 127
<212> TYPE: PRT
<213> ORGANISM: Homo sapiens
<220> FEATURE:
<221> NAME/KEY: UNSURE
<222> LOCATION: (70)..(70)
<223> OTHER INFORMATION: Xaa at position 70 is either Arg or Gly
<221> NAME/KEY: UNSURE
<222> LOCATION: (91)..(91)
<223> OTHER INFORMATION: Xaa at position 91 is either Lys or Asn

<400> SEQUENCE: 1

Met Gln Gln Arg Gly Leu Ala Ile Val Ala Leu Ala Val Cys Ala Ala
1               5                   10                  15

Leu His Ala Ser Glu Ala Ile Leu Pro Ile Ala Ser Ser Cys Cys Thr
            20                  25                  30

Glu Val Ser His His Ile Ser Arg Arg Leu Leu Glu Arg Val Asn Met
        35                  40                  45

Cys Arg Ile Gln Arg Ala Asp Gly Asp Cys Asp Leu Ala Ala Val Ile
    50                  55                  60

Leu His Val Lys Arg Xaa Arg Ile Cys Val Ser Pro His Asn His Thr
65                  70                  75                  80

Val Lys Gln Trp Met Lys Val Gln Ala Ala Xaa Lys Asn Gly Lys Gly
                85                  90                  95

Asn Val Cys His Arg Lys Lys His His Gly Lys Arg Asn Ser Asn Arg
            100                 105                 110

Ala His Gln Gly Lys His Glu Thr Tyr Gly His Lys Thr Pro Tyr
        115                 120                 125

```
<210> SEQ ID NO 2
<211> LENGTH: 104
<212> TYPE: PRT
<213> ORGANISM: Homo sapiens
<220> FEATURE:
<221> NAME/KEY: UNSURE
<222> LOCATION: (47)..(47)
<223> OTHER INFORMATION: Xaa at position 47 is either Arg or Gly
<221> NAME/KEY: UNSURE
<222> LOCATION: (68)..(68)
<223> OTHER INFORMATION: Xaa at position 68 is either Lys or Asn

<400> SEQUENCE: 2

Leu Pro Ile Ala Ser Ser Cys Cys Thr Glu Val Ser His His Ile Ser
 1               5                  10                  15

Arg Arg Leu Leu Glu Arg Val Asn Met Cys Arg Ile Gln Arg Ala Asp
             20                  25                  30

Gly Asp Cys Asp Leu Ala Ala Val Ile Leu His Val Lys Arg Xaa Arg
         35                  40                  45

Ile Cys Val Ser Pro His Asn His Thr Val Lys Gln Trp Met Lys Val
     50                  55                  60

Gln Ala Ala Xaa Lys Asn Gly Lys Gly Asn Val Cys His Arg Lys Lys
 65                  70                  75                  80

His His Gly Lys Arg Asn Ser Asn Arg Ala His Gln Gly Lys His Glu
                 85                  90                  95

Thr Tyr Gly His Lys Thr Pro Tyr
                100

<210> SEQ ID NO 3
<211> LENGTH: 18
<212> TYPE: PRT
<213> ORGANISM: Homo sapiens

<400> SEQUENCE: 3

Thr Glu Val Ser His His Ile Ser Arg Arg Leu Leu Glu Arg Val Asn
 1               5                  10                  15

Met Cys

<210> SEQ ID NO 4
<211> LENGTH: 16
<212> TYPE: PRT
<213> ORGANISM: Homo sapiens

<400> SEQUENCE: 4

Lys Asn Gly Lys Gly Asn Val Cys His Arg Lys Lys His His Gly Lys
 1               5                  10                  15

<210> SEQ ID NO 5
<211> LENGTH: 19
<212> TYPE: PRT
<213> ORGANISM: Homo sapiens

<400> SEQUENCE: 5

Asn Ser Asn Arg Ala His Gln Gly Lys His Glu Thr Tyr Gly His Lys
 1               5                  10                  15

Thr Pro Tyr

<210> SEQ ID NO 6
<211> LENGTH: 3117
<212> TYPE: DNA
<213> ORGANISM: Homo sapiens
<220> FEATURE:
```

<221> NAME/KEY: unsure
<222> LOCATION: (1)..(3117)
<223> OTHER INFORMATION: n at any position in the sequence represents a or g or c or t/u
<221> NAME/KEY: unsure
<222> LOCATION: (1)..(3117)
<223> OTHER INFORMATION: y at any position in the sequence represents t/u or c
<221> NAME/KEY: unsure
<222> LOCATION: (1)..(3117)
<223> OTHER INFORMATION: m at any position in the sequence represents a or c
<221> NAME/KEY: unsure
<222> LOCATION: (1)..(3117)
<223> OTHER INFORMATION: k at any position in the sequence represents g or t/u
<221> NAME/KEY: unsure
<222> LOCATION: (1)..(3117)
<223> OTHER INFORMATION: s at any position in the sequence represents g or c
<221> NAME/KEY: unsure
<222> LOCATION: (1)..(3117)
<223> OTHER INFORMATION: w at any position in the sequence represents a or t/u
<221> NAME/KEY: unsure
<222> LOCATION: (1)..(3117)
<223> OTHER INFORMATION: r at any position in the sequence represents g or a

<400> SEQUENCE: 6

```
aacatcctca cttgtgttgc tgtcagtgcc tgtanggcag gcaggaatgc agcagagagg      60
actcgccatc gtggccttgg ctgtctgtgc ggccctacat gcctcagaag ccatacttcc     120
cattgcctcc agctgttgca cggaggtttc acatcatatt tccagaaggc tcctggaaag     180
agtgaatatg tgtcgcatcc agagagctga tggggattgt gacttggctg ctgtcatcct     240
tcatgtcaag cgcngaagaa tctgtgtcag cccgcacaac catactgtta agcagtggat     300
gaaagtgcaa gctgccaana aaatggtaa aggaaatgtt tgccacagga agaaacacca     360
tggcaagagg aacagtaaca gggcacatca ggggaaacac gaaacatacg gccataaaac     420
tccttattag agaatctaca gataaatcta cagagacaat cccccaagtg gacttggcca     480
tgattggttg taagtttatc atctgaattc tccttattgt agacaacaga acaaaacaaa     540
atattggttt ttaaaaaatg aacaattgtg ccgtatgcaa atgtacccaa taatatactc     600
cactggaaaa tgaaatgaaa aaanntatact ggctgggtat ggtgggtccc ccttttatc      660
ccannnnctt cgggaggcag aggcaggagg atcacttgag accaggantt ngagacnagc     720
tngggcaaa anagcaanga cntcattnt acaaacnaaa aaaaannttg gcccggcntg     780
gtagnacttg cntataatcc cagcnacatg ggaggtngag gtgggaggat cacttgagtc     840
tgggngagtt ngaggtngca gtgagcagcn tgggtgacag aatgnagacc ntgtctctaa     900
aaataataat aataatgata gtgtatatct tcatataata ttttaagnag gagcatatag     960
ataaacttn ctcccaactt tttaattata gttttccaaa cttacagaga agttaaagaa    1020
atggtacaat gaacatctat atatctttca ccacaatatt aatcattgtt aatattgtgc    1080
cacattgct ttctctctcc tctcttggta ggggttncaa tataaaatat tataactttt    1140
aaatatatc ttgttttgct aaccattgga aaataagttg caaaaatcat gacacttcac    1200
ccctagtttc ttttnggtgt tataacttga catacccta aataaagaca ttttctaca    1260
taatcacctt atcagttta tacctaaaaa attaataatt tcatctaata tattccatat    1320
tcaaattttc ccaactattt agagagcatt ttatgtagtt tttttttcac tccagtaatc    1380
aatcaaggtn gacatacata ttgcaaataa ttgttatttt tctttaatat ctttcaatct    1440
```

```
aagaaagttc ctctgtcttt tttttttaat tttaaaatt attttgttga gggagggtct    1500
tgctgtgtct tccaggctgg agtgcagtgg cacaattttg attttggctc actgaagcct    1560
caactttagg gctcaagcaa tcctcccacc tcagcctncc cgagtatctg ggatcaaggt    1620
gcatacccac cacacctggc taattttgtt tattttttgt agagacaggg tctcactatg    1680
ttgcccaggt tgatctcaaa ctcctgggct caagcgatcc tcccaccttg gcctcccaaa    1740
gtactgggat tataggtgtg agccacagtg cctggcctaa ttattttctt gtgatcaaat    1800
tcaggtttaa tgttttggt taagaatttc ctacgtgaat tcgtgtactt attttgtcat    1860
ttagagttca taaatattag ggtttatttt ctaaatagaa tagtttaaac taaatataac    1920
ttcaaaacgt ctagtttgag tagctaccgt tgtttggatt gaaatttttct gatactgaaa    1980 agaacaaaaa gcctgccttt ctgcccanaa csnnttgcyt cccccagtna gttcttggng    2040
cagnactagt tagggnccca gagttnggcc ttnngkgtgg tgattttang ytctgcctaa    2100
acaaggngcn wacatytttt agctcctatt ccaccyttct namamgtttt tgttgtkgtt    2160
tgnttgtttt tttkgagaca grrtntnayt ctgtttgccc argctggart tgcagtggca    2220
caatytnggy tncattgcaa cytcngcytc cssgccgttc aaktgatyyt cttgcytcag    2280
cytccccaag taantgatat tacaggngcc cagccaccam acccgntga wttttgtatt    2340 tttartarar amrggttttt cccgcnttgg cngggctggc tcnaantcc ttgamctcna    2400 ktgaaccacc cgcctgtgcc ycccaaantg ctggaattac cancgttgan ccaccatgcc    2460
gggcycacac gtttgarttt ganaccattg tnccattcct cttttggcct yttttttntc    2520
catagnngct tcaagataga tangtaagrg cccagtagtn gttcwtarga agcnmatagr    2580
rancrggarc canttttnatc aggtgggcag gtgtccnngg cytccctgct ggytnntccc    2640
aagcggtggt gttgccarga nktnttggar gtgataatgg gananaccag naggcmctga    2700
gtyncnntag gttnaaatgc caccaaaact ggcctttggc ctaatatccy ycnttgamta    2760
nttarcattt awtttattwa tttncctgac atttntgcma nccttttgtwt ttntatttcc    2820 nctntatara wgargaaatt tgaggntytt araggtaaaa tganttgcnc nrgtnnacmc    2880
aggaagtggc nraranaanc tttttanatn mgaaaaaatt aataaaatat aatatgagag    2940
taacttaaaa tattaataaa ccacaatttt aaattaatta accgtgataa ccaacattaa    3000
taaaagttaa gataccaaaa cactggtgtn taattttttn aactaacaan ttgaattatt    3060
ttccatttta aattaattaa ccgtgataac caacattaat aaaagttaag ataccgn       3117
```

<210> SEQ ID NO 7
<211> LENGTH: 381
<212> TYPE: DNA
<213> ORGANISM: Homo sapiens
<220> FEATURE:
<221> NAME/KEY: unsure
<222> LOCATION: (208)..(208)
<223> OTHER INFORMATION: n may represent a or g or c or t/u
<221> NAME/KEY: unsure
<222> LOCATION: (273)..(273)
<223> OTHER INFORMATION: n may represent a or g or c or t/u

<400> SEQUENCE: 7

```
atgcagcaga gaggactcgc catcgtggcc ttggctgtct gtgcggccct acatgcctca      60
gaagccatac ttcccattgc ctccagctgt tgcacggagg tttcacatca tatttccaga     120
aggtccctgg aaagagtgaa tatgtgtcgc atccagagag ctgatgggga ttgtgacttg     180
gctgctgtca tccttcatgt caagcgcnga agaatctgtg tcagcccgca caaccatact     240
```

```
gttaagcagt ggatgaaagt gcaagctgcc aanaaaaatg gtaaaggaaa tgtttgccac      300
aggaagaaac accatggcaa gaggaacagt aacagggcac atcagggaaa acacgaaaca      360
tacggccata aaactcctta t                                                381

<210> SEQ ID NO 8
<211> LENGTH: 104
<212> TYPE: DNA
<213> ORGANISM: Homo sapiens

<400> SEQUENCE: 8
acacgaattc acgtaggaaa ttcttaacca aaaacattaa acctgaattt gatcacaaga       60
aaataattag gccaggcact gtggctcaca cctataatcc cagt                      104

<210> SEQ ID NO 9
<211> LENGTH: 25
<212> TYPE: DNA
<213> ORGANISM: Homo sapiens

<400> SEQUENCE: 9
gaattcacgt aggaaattct taacc                                            25

<210> SEQ ID NO 10
<211> LENGTH: 22
<212> TYPE: DNA
<213> ORGANISM: Homo sapiens

<400> SEQUENCE: 10
actgggatta taggtgtgag cc                                               22

<210> SEQ ID NO 11
<211> LENGTH: 311
<212> TYPE: DNA
<213> ORGANISM: Homo sapiens
<220> FEATURE:
<221> NAME/KEY: unsure
<222> LOCATION: (101)..(101)
<223> OTHER INFORMATION: n may be a or g or c or t/u
<221> NAME/KEY: unsure
<222> LOCATION: (162)..(162)
<223> OTHER INFORMATION: n may be a or g or c or t/u

<400> SEQUENCE: 11
ggagagagcc gtatgtttcg tgtttcccct gatgtgccct gttactgttc ctcttgccat       60
ggtgtttctt cctgtggcaa acatttcctt taccattttt nttggcagct tgcactttca     120
tccactgctt aacagtatgg ttgtgcgggc tgacacagat tnttctgcgc ttgacatgaa     180
ggatgacagc agccaagtca caatccccat cagctctctg gatgcgacac atattcactc     240
tttccaggag ccttctggaa atatgatgtg aaacctccgt gcaacagctg gaggcaatgg     300
gaagtatggc t                                                         311

<210> SEQ ID NO 12
<211> LENGTH: 20
<212> TYPE: DNA
<213> ORGANISM: Artificial sequence
<220> FEATURE:
<223> OTHER INFORMATION: Sequencing primer T7

<400> SEQUENCE: 12
taatacgact cactataggg                                                  20

<210> SEQ ID NO 13
```

```
<211> LENGTH: 18
<212> TYPE: DNA
<213> ORGANISM: Artificial sequence
<220> FEATURE:
<223> OTHER INFORMATION: pCR3.1 Reverse Primer

<400> SEQUENCE: 13
tagaaggcac agtcgagg                                                   18

<210> SEQ ID NO 14
<211> LENGTH: 22
<212> TYPE: DNA
<213> ORGANISM: Artificial sequence
<220> FEATURE:
<223> OTHER INFORMATION: Gene specific primer (24R)

<400> SEQUENCE: 14
actgggatta taggtgtgag cc                                              22

<210> SEQ ID NO 15
<211> LENGTH: 24
<212> TYPE: DNA
<213> ORGANISM: Artificial sequence
<220> FEATURE:
<223> OTHER INFORMATION: Gene specific primer (24R2)

<400> SEQUENCE: 15
caaattcagg tttaatgttt ttgg                                            24

<210> SEQ ID NO 16
<211> LENGTH: 21
<212> TYPE: DNA
<213> ORGANISM: Artificial sequence
<220> FEATURE:
<223> OTHER INFORMATION: Gene specific primer (F4 )

<400> SEQUENCE: 16
ctcaaacgtg tgagcccggc a                                               21

<210> SEQ ID NO 17
<211> LENGTH: 25
<212> TYPE: DNA
<213> ORGANISM: Artificial sequence
<220> FEATURE:
<223> OTHER INFORMATION: Gene specific primer (F3)

<400> SEQUENCE: 17
gctactcaaa ctagacgttt tgaag                                           25

<210> SEQ ID NO 18
<211> LENGTH: 24
<212> TYPE: DNA
<213> ORGANISM: Artificial sequence
<220> FEATURE:
<223> OTHER INFORMATION: primers F8

<400> SEQUENCE: 18
ccgtatgttt cgtgtttccc ctga                                            24

<210> SEQ ID NO 19
<211> LENGTH: 24
<212> TYPE: DNA
<213> ORGANISM: Artificial sequence
<220> FEATURE:
<223> OTHER INFORMATION: Primer R5

<400> SEQUENCE: 19
```
agccatactt cccattgcct ccag     24

<210> SEQ ID NO 20
<211> LENGTH: 150
<212> TYPE: PRT
<213> ORGANISM: Homo sapiens

<400> SEQUENCE: 20

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Met Gln Thr Phe Gln Ala Gly Pro His
            100                 105                 110

Ala Val Lys Lys Leu Ser Ser Gly Asn Ser Lys Leu Ser Ser Ser Lys
        115                 120                 125

Phe Ser Asn Pro Ile Ser Ser Ser Lys Arg Asn Val Ser Leu Leu Ile
    130                 135                 140

Ser Ala Asn Ser Gly Leu
145                 150

<210> SEQ ID NO 21
<211> LENGTH: 95
<212> TYPE: PRT
<213> ORGANISM: Homo sapiens

<400> SEQUENCE: 21

Met Cys Cys Thr Lys Ser Leu Leu Leu Ala Ala Leu Met Ser Val Leu
1               5                   10                  15

Leu Leu His Leu Cys Gly Glu Ser Glu Ala Ser Asn Phe Asp Cys Cys
            20                  25                  30

Leu Gly Tyr Thr Asp Arg Ile Leu His Pro Lys Phe Ile Val Gly Phe
        35                  40                  45

Thr Arg Gln Leu Ala Asn Glu Gly Cys Asp Ile Asn Ala Ile Ile Phe
    50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Lys Val Lys Asn Met
                85                  90                  95

<210> SEQ ID NO 22
<211> LENGTH: 94
<212> TYPE: PRT
<213> ORGANISM: Homo sapiens

<400> SEQUENCE: 22

Met Ala Pro Leu Lys Met Leu Ala Leu Val Thr Leu Leu Leu Gly Ala
1               5                   10                  15

Ser Leu Gln His Ile His Ala Ala Arg Gly Thr Asn Val Gly Arg Glu

```
                    20                  25                  30

Cys Cys Leu Glu Tyr Phe Lys Gly Ala Ile Pro Leu Arg Lys Leu Lys
            35                  40                  45

Thr Trp Tyr Gln Thr Ser Glu Asp Cys Ser Arg Asp Ala Ile Val Phe
 50                  55                  60

Val Thr Val Gln Gly Arg Ala Ile Cys Ser Asp Pro Asn Asn Gln Arg
 65                  70                  75                  80

Val Lys Asn Ala Val Lys Tyr Leu Gln Ser Leu Glu Arg Ser
                 85                  90

<210> SEQ ID NO 23
<211> LENGTH: 96
<212> TYPE: PRT
<213> ORGANISM: Homo sapiens

<400> SEQUENCE: 23

Met Gln Ile Ile Thr Thr Ala Leu Val Cys Leu Leu Leu Ala Gly Met
 1               5                  10                  15

Trp Pro Glu Asp Val Asp Ser Lys Ser Met Gln Val Pro Phe Ser Arg
                 20                  25                  30

Cys Cys Phe Ser Phe Ala Glu Gln Glu Ile Pro Leu Arg Ala Ile Leu
            35                  40                  45

Cys Tyr Arg Asn Thr Ser Ser Ile Cys Ser Asn Glu Gly Leu Ile Phe
 50                  55                  60

Lys Leu Lys Arg Gly Lys Glu Ala Cys Ala Leu Asp Thr Val Gly Trp
 65                  70                  75                  80

Val Gln Arg His Arg Lys Met Leu Arg His Cys Pro Ser Lys Arg Lys
                 85                  90                  95

<210> SEQ ID NO 24
<211> LENGTH: 77
<212> TYPE: PRT
<213> ORGANISM: Homo sapiens

<400> SEQUENCE: 24

Ala Gln Pro Asp Ser Val Ser Ile Pro Ile Thr Cys Cys Phe Asn Val
 1               5                  10                  15

Ile Asn Arg Lys Ile Pro Ile Gln Arg Leu Glu Ser Tyr Thr Arg Ile
                 20                  25                  30

Thr Asn Ile Gln Cys Pro Lys Glu Ala Val Ile Phe Lys Thr Lys Arg
            35                  40                  45

Gly Lys Glu Val Cys Ala Asp Pro Lys Glu Arg Trp Val Arg Asp Ser
 50                  55                  60

Met Lys His Leu Asp Gln Ile Phe Gln Asn Leu Lys Pro
 65                  70                  75

<210> SEQ ID NO 25
<211> LENGTH: 98
<212> TYPE: PRT
<213> ORGANISM: Homo sapiens

<400> SEQUENCE: 25

Met Lys Val Ser Ala Val Leu Leu Cys Leu Leu Leu Met Thr Ala Ala
 1               5                  10                  15

Phe Asn Pro Gln Gly Leu Ala Gln Pro Asp Ala Leu Asn Val Pro Ser
                 20                  25                  30

Thr Cys Cys Phe Thr Phe Ser Ser Lys Lys Ile Ser Leu Gln Arg Leu
            35                  40                  45
```

```
Lys Ser Tyr Val Ile Thr Thr Ser Arg Cys Pro Gln Lys Ala Val Ile
         50                  55                  60

Phe Arg Thr Lys Leu Gly Lys Glu Ile Cys Ala Asp Pro Lys Glu Lys
 65                  70                  75                  80

Trp Val Gln Asn Tyr Met Lys His Leu Gly Arg Lys Ala His Thr Leu
                 85                  90                  95

Lys Thr

<210> SEQ ID NO 26
<211> LENGTH: 97
<212> TYPE: PRT
<213> ORGANISM: Homo sapiens

<400> SEQUENCE: 26

Met Lys Val Ser Ala Ala Leu Leu Trp Leu Leu Ile Ala Ala Ala
 1               5                  10                  15

Phe Ser Pro Gln Gly Leu Ala Gly Pro Ala Ser Val Pro Thr Thr Cys
                 20                  25                  30

Cys Phe Asn Leu Ala Asn Arg Lys Ile Pro Leu Gln Arg Leu Glu Ser
             35                  40                  45

Tyr Arg Arg Ile Thr Ser Gly Lys Cys Pro Gln Lys Ala Val Ile Phe
         50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                 85                  90                  95

Pro

<210> SEQ ID NO 27
<211> LENGTH: 99
<212> TYPE: PRT
<213> ORGANISM: Homo sapiens

<400> SEQUENCE: 27

Met Lys Ala Ser Ala Ala Leu Leu Cys Leu Leu Thr Ala Ala Ala
 1               5                  10                  15

Phe Ser Pro Gln Gly Leu Ala Gln Pro Val Gly Ile Asn Thr Ser Thr
                 20                  25                  30

Thr Cys Cys Tyr Arg Phe Ile Asn Lys Lys Ile Pro Lys Gln Arg Leu
             35                  40                  45

Glu Ser Tyr Arg Arg Thr Thr Ser Ser His Cys Pro Arg Glu Ala Val
         50                  55                  60

Ile Phe Lys Thr Lys Leu Asp Lys Glu Asp Cys Ala Asp Pro Thr Gln
 65                  70                  75                  80

Lys Trp Val Gln Asp Pro Met Lys His Leu Asp Lys Lys Thr Gln Thr
                 85                  90                  95

Pro Lys Leu

<210> SEQ ID NO 28
<211> LENGTH: 99
<212> TYPE: PRT
<213> ORGANISM: Homo sapiens

<400> SEQUENCE: 28

Met Lys Val Ser Ala Ala Leu Leu Cys Leu Leu Thr Ala Ala Ala
 1               5                  10                  15
```

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Asp Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 29
<211> LENGTH: 91
<212> TYPE: PRT
<213> ORGANISM: Homo sapiens

<400> SEQUENCE: 29

Met Lys Val Ser Ala Ala Arg Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 30
<211> LENGTH: 93
<212> TYPE: PRT
<213> ORGANISM: Homo sapiens

<400> SEQUENCE: 30

Met Lys Ile Ser Val Ala Ala Ile Pro Phe Phe Leu Leu Ile Thr Ile
1               5                   10                  15

Ala Leu Gly Thr Lys Thr Glu Ser Ser Ser Arg Gly Pro Tyr His Pro
                20                  25                  30

Ser Glu Cys Cys Phe Thr Tyr Thr Thr Tyr Lys Ile Pro Arg Gln Arg
            35                  40                  45

Ile Met Asp Tyr Tyr Glu Thr Asn Ser Gln Cys Ser Lys Pro Gly Ile
    50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90

<210> SEQ ID NO 31
<211> LENGTH: 92
<212> TYPE: PRT
<213> ORGANISM: Homo sapiens

<400> SEQUENCE: 31

Met Lys Leu Cys Val Thr Val Leu Ser Leu Leu Met Leu Val Ala Ala
1               5                   10                  15

-continued

```
Phe Cys Ser Pro Ala Leu Ser Ala Pro Met Gly Ser Asp Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90
```

<210> SEQ ID NO 32
<211> LENGTH: 93
<212> TYPE: PRT
<213> ORGANISM: Homo sapiens

<400> SEQUENCE: 32

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90
```

<210> SEQ ID NO 33
<211> LENGTH: 92
<212> TYPE: PRT
<213> ORGANISM: Homo sapiens

<400> SEQUENCE: 33

```
Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90
```

<210> SEQ ID NO 34
<211> LENGTH: 89
<212> TYPE: PRT
<213> ORGANISM: Homo sapiens

<400> SEQUENCE: 34

```
Met Lys Gly Leu Ala Ala Ala Leu Leu Val Leu Val Cys Thr Met Ala
1               5                   10                  15
```

-continued

```
Leu Cys Ser Cys Ala Gln Val Gly Thr Asn Lys Glu Leu Cys Cys Leu
            20                  25                  30

Val Tyr Thr Ser Trp Gln Ile Pro Gln Lys Phe Ile Val Asp Tyr Ser
            35                  40                  45

Glu Thr Ser Pro Gln Cys Pro Lys Pro Gly Val Ile Leu Leu Thr Lys
        50                  55                  60

Arg Gly Arg Gln Asp Cys Ala Asp Pro Asn Lys Lys Trp Val Gln Lys
65                  70                  75                  80

Tyr Ile Ser Asp Leu Lys Leu Asn Ala
                85

<210> SEQ ID NO 35
<211> LENGTH: 104
<212> TYPE: DNA
<213> ORGANISM: Homo sapiens

<400> SEQUENCE: 35
acacgaattc acgtaggaaa ttcttaacca aaaacattaa acctgaattt gatcacaaga      60
aaataattag gccaggcact gtggctcaca cctataatcc cagt                     104
```